United States Patent
Charr et al.

(10) Patent No.: US 11,194,317 B2
(45) Date of Patent: Dec. 7, 2021

(54) REMOTE MONITORING OF CHLORIDE TREATERS USING A PROCESS SIMULATOR BASED CHLORIDE DISTRIBUTION ESTIMATE

(71) Applicant: UOP LLC, Des Plaines, IL (US)

(72) Inventors: Jorge Charr, Northbrook, IL (US); Dean E. Rende, Arlington Heights, IL (US); Bryan James Egolf, Crystal Lake, IL (US); Yue Zhu, Glenview, IL (US); Mary Wier, Schaumburg, IL (US); Guy Woodle, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 408 days.

(21) Appl. No.: 16/148,763

(22) Filed: Oct. 1, 2018

(65) Prior Publication Data

US 2019/0101907 A1 Apr. 4, 2019

Related U.S. Application Data

(60) Provisional application No. 62/566,736, filed on Oct. 2, 2017.

(51) Int. Cl.
*G05B 19/418* (2006.01)
*G08B 21/18* (2006.01)
(Continued)

(52) U.S. Cl.
CPC .......... *G05B 19/41885* (2013.01); *C07C 7/10* (2013.01); *C10G 35/24* (2013.01);
(Continued)

(58) Field of Classification Search
CPC ........... G05B 2219/32234; G05B 2219/42155; G05B 17/02; G05B 19/41885; G08B 21/18; C10G 35/24; C10G 45/02; C07C 7/10
See application file for complete search history.

(56) References Cited

U.S. PATENT DOCUMENTS

| | | | |
|---|---|---|---|
| 4,159,239 A | 6/1979 | Schwartz | 208/113 |
| 4,267,458 A | 5/1981 | Uram | 290/40 R |

(Continued)

FOREIGN PATENT DOCUMENTS

| | | | | |
|---|---|---|---|---|
| EP | 0181744 A1 | 5/1986 | | B65G 53/66 |
| EP | 2746884 A1 | 6/2014 | | G05B 23/02 |

(Continued)

OTHER PUBLICATIONS

International Preliminary Report on Patentability for PCT/US2018/053945, dated Apr. 8, 2020.
(Continued)

*Primary Examiner* — Shogo Sasaki

(57) ABSTRACT

Catalysts used for catalytic reforming are treated with organic chloride to condition the catalysts. Chloride treaters may be located in the product streams to remove the chloride contaminants. The continuous catalyst reforming process, including the catalyst reformer unit and chloride treaters, may be monitored in order to predict when adsorbent replacement or regeneration is needed. For example, one or more sensors and measurement devices may be used to monitor certain conditions or parameters. A system may be configured to take one or more actions in response to certain conditions or parameters being met.

7 Claims, 11 Drawing Sheets

(51) Int. Cl.
  *C07C 7/10*     (2006.01)
  *C10G 45/02*    (2006.01)
  *C10G 35/24*    (2006.01)

(52) U.S. Cl.
  CPC ............ *C10G 45/02* (2013.01); *G08B 21/18* (2013.01); *G05B 2219/32234* (2013.01); *G05B 2219/42155* (2013.01)

(56) References Cited

U.S. PATENT DOCUMENTS

| | | | | |
|---|---|---|---|---|
| 4,284,494 A | 8/1981 | Bartholic | | 208/164 |
| 4,362,614 A | 12/1982 | Asdigian | | 208/235 |
| 4,380,146 A | 4/1983 | Yannone | | 60/39.281 |
| 4,385,985 A | 5/1983 | Gross | | 208/113 |
| 4,411,773 A | 10/1983 | Gross | | 208/159 |
| 4,709,546 A | 12/1987 | Weiler | | 415/116 |
| 4,775,460 A | 10/1988 | Reno | | |
| 4,795,545 A | 1/1989 | Schmidt | | |
| 4,902,469 A | 2/1990 | Watson | | 376/216 |
| 5,077,252 A | 12/1991 | Owen et al. | | 502/43 |
| 5,227,121 A | 7/1993 | Scarola | | 340/525 |
| 5,582,684 A | 12/1996 | Holmqvist et al. | | 162/49 |
| 5,605,435 A | 2/1997 | Haugen | | 137/514 |
| 5,614,644 A * | 3/1997 | Liang | | C07D 307/08 549/507 |
| 5,616,214 A | 4/1997 | Leclerc | | 162/49 |
| 5,642,296 A | 6/1997 | Saxena | | 216/84 |
| 5,666,297 A | 9/1997 | Britt et al. | | 364/578 |
| 5,705,730 A * | 1/1998 | Zarchy | | C07C 5/277 585/737 |
| 5,792,897 A * | 8/1998 | Rosser, Jr. | | C10G 25/02 208/140 |
| 5,817,517 A | 10/1998 | Perry et al. | | 436/55 |
| 5,928,500 A * | 7/1999 | Richard | | C10G 25/003 208/262.1 |
| 6,038,540 A | 3/2000 | Krist et al. | | 705/8 |
| 6,081,230 A | 6/2000 | Hoshino | | 342/357.32 |
| 6,230,486 B1 | 5/2001 | Yasui | | 123/674 |
| 6,266,605 B1 | 7/2001 | Yasui | | 60/276 |
| 6,271,845 B1 | 8/2001 | Richardson | | 715/764 |
| 6,392,114 B1 | 5/2002 | Shields et al. | | 582/719 |
| 6,760,716 B1 | 7/2004 | Ganesamoorthi et al. | | 706/21 |
| 6,772,044 B1 | 8/2004 | Mathur et al. | | 700/204 |
| 6,795,798 B2 | 9/2004 | Eryurek et al. | | 702/188 |
| 6,982,032 B2 | 1/2006 | Shaffer et al. | | 210/101 |
| 6,983,227 B1 | 1/2006 | Thalhammer-Reyero | | |
| 7,006,889 B2 | 2/2006 | Mathur et al. | | 700/204 |
| 7,067,333 B1 | 6/2006 | Pasadyn et al. | | 438/5 |
| 7,133,807 B2 | 11/2006 | Karasawa | | 702/188 |
| 7,151,966 B1 | 12/2006 | Baier et al. | | 700/19 |
| 7,246,039 B2 | 7/2007 | Moorhouse | | 702/185 |
| 7,313,447 B2 | 12/2007 | Hsuing et al. | | 700/9 |
| 7,415,357 B1 | 8/2008 | Stluka et al. | | 702/6 |
| 7,567,887 B2 | 7/2009 | Emigholz et al. | | 702/182 |
| 7,742,833 B1 | 6/2010 | Herbst et al. | | 700/108 |
| 7,836,941 B2 | 11/2010 | Song et al. | | |
| 7,877,596 B2 | 1/2011 | Kune et al. | | 713/153 |
| 7,925,979 B2 | 4/2011 | Forney et al. | | 715/733 |
| 7,936,878 B2 | 5/2011 | Kune et al. | | 380/270 |
| 7,979,192 B2 | 7/2011 | Morrison et al. | | |
| 7,995,526 B2 | 8/2011 | Liu et al. | | 370/329 |
| 8,050,889 B2 | 11/2011 | Fluegge et al. | | 702/182 |
| 8,055,371 B2 | 11/2011 | Sanford et al. | | 700/108 |
| 8,111,619 B2 | 2/2012 | Liu et al. | | 370/229 |
| 8,128,808 B2 | 3/2012 | Hassan et al. | | 208/209 |
| 8,204,717 B2 | 6/2012 | McLaughlin et al. | | 702/188 |
| 8,244,384 B2 | 8/2012 | Pachner et al. | | 700/30 |
| 8,280,057 B2 | 10/2012 | Budampati et al. | | 380/270 |
| 8,352,049 B2 | 1/2013 | Hsiung et al. | | |
| 8,354,081 B2 | 1/2013 | Wheat et al. | | |
| 8,385,436 B2 | 2/2013 | Holm et al. | | 375/260 |
| 8,428,067 B2 | 4/2013 | Budampati et al. | | 370/395.21 |
| 8,458,778 B2 | 6/2013 | Budampati et al. | | 726/6 |
| 8,571,064 B2 | 10/2013 | Kore et al. | | 370/469 |
| 8,630,962 B2 | 1/2014 | Maeda | | 706/12 |
| 8,644,192 B2 | 2/2014 | Budampati et al. | | 370/255 |
| 8,811,231 B2 | 8/2014 | Budampati et al. | | 370/255 |
| 8,815,152 B2 | 8/2014 | Burgess et al. | | |
| 8,923,882 B2 | 12/2014 | Gandhi et al. | | 455/455 |
| 8,926,737 B2 | 1/2015 | Chatterjee et al. | | |
| 9,053,260 B2 | 6/2015 | Romatier et al. | | |
| 9,134,717 B2 | 9/2015 | Trnka | | |
| 9,166,667 B2 | 10/2015 | Thanikachalam | | |
| 9,176,498 B2 | 11/2015 | Baramov | | |
| 9,354,631 B2 | 5/2016 | Mohideen et al. | | |
| 9,571,919 B2 | 2/2017 | Zhang et al. | | |
| 9,580,341 B1 | 2/2017 | Brown et al. | | C02F 3/006 |
| 9,751,817 B2 | 9/2017 | Jani et al. | | |
| 9,864,823 B2 | 1/2018 | Horn et al. | | |
| 9,968,899 B1 | 5/2018 | Gellaboina et al. | | |
| 10,095,200 B2 | 10/2018 | Horn et al. | | |
| 10,107,295 B1 | 10/2018 | Brecheisen | | |
| 10,180,680 B2 | 1/2019 | Horn et al. | | |
| 10,183,266 B2 | 1/2019 | Victor et al. | | |
| 10,222,787 B2 | 3/2019 | Romatier et al. | | |
| 10,328,408 B2 | 6/2019 | Victor et al. | | |
| 2002/0123864 A1 | 9/2002 | Eryurek et al. | | 702/188 |
| 2002/0179495 A1 | 12/2002 | Heyse et al. | | 208/137 |
| 2003/0036052 A1 | 2/2003 | Delwiche et al. | | 435/4 |
| 2003/0105775 A1 | 6/2003 | Shimada | | |
| 2003/0147351 A1 | 8/2003 | Greenlee | | 370/232 |
| 2003/0223918 A1 | 12/2003 | Cammy | | 422/144 |
| 2004/0079392 A1 | 4/2004 | Kuechler | | 134/22.19 |
| 2004/0099572 A1 | 5/2004 | Evans | | 208/113 |
| 2004/0109788 A1 | 6/2004 | Li et al. | | 422/3 |
| 2004/0122273 A1 | 6/2004 | Kabin | | 585/639 |
| 2004/0122936 A1 | 6/2004 | Mizelle et al. | | |
| 2004/0147036 A1 | 7/2004 | Krenn et al. | | 436/119 |
| 2004/0148144 A1 | 7/2004 | Martin | | |
| 2004/0204775 A1 | 10/2004 | Keyes et al. | | 705/30 |
| 2004/0204913 A1 | 10/2004 | Mueller et al. | | |
| 2004/0220689 A1 | 11/2004 | Mathur et al. | | 700/97 |
| 2004/0220778 A1 | 11/2004 | Imai et al. | | 702/188 |
| 2005/0027721 A1 | 2/2005 | Saenz | | 707/100 |
| 2005/0029163 A1 | 2/2005 | Letzsch | | 208/113 |
| 2005/0133211 A1 | 6/2005 | Osborn et al. | | |
| 2005/0216209 A1 | 9/2005 | Evans | | 702/45 |
| 2006/0020423 A1 | 1/2006 | Sharpe, Jr. | | 702/183 |
| 2006/0133412 A1 | 6/2006 | Callaghan | | 370/465 |
| 2006/0252642 A1 | 11/2006 | Kanazirev | | |
| 2006/0259163 A1 | 11/2006 | Hsiung et al. | | 700/30 |
| 2007/0020154 A1 | 1/2007 | Evans | | 422/139 |
| 2007/0059159 A1 | 3/2007 | Hjerpe | | 415/117 |
| 2007/0059838 A1 | 3/2007 | Morrison et al. | | 436/55 |
| 2007/0091824 A1 | 4/2007 | Budampati et al. | | 370/255 |
| 2007/0091825 A1 | 4/2007 | Budampati et al. | | 370/255 |
| 2007/0185664 A1 | 8/2007 | Tanaka et al. | | 702/56 |
| 2007/0192078 A1 | 8/2007 | Nasle et al. | | 703/14 |
| 2007/0212790 A1 | 9/2007 | Welch et al. | | 436/139 |
| 2007/0250292 A1 | 10/2007 | Alagappan et al. | | 702/184 |
| 2007/0260656 A1 | 11/2007 | Wiig | | |
| 2007/0271452 A1 | 11/2007 | Kune et al. | | 713/150 |
| 2008/0086322 A1 | 4/2008 | Wallace | | 705/1 |
| 2008/0130902 A1 | 6/2008 | Kune et al. | | 380/286 |
| 2008/0154434 A1 | 6/2008 | Galloway et al. | | |
| 2008/0217005 A1 | 9/2008 | Stluka et al. | | 166/250.01 |
| 2008/0282606 A1 | 11/2008 | Plaza et al. | | |
| 2009/0059786 A1 | 3/2009 | Budampati et al. | | 370/230 |
| 2009/0060192 A1 | 3/2009 | Budampati et al. | | 380/270 |
| 2009/0064295 A1 | 3/2009 | Budampati et al. | | 726/6 |
| 2009/0201899 A1 | 8/2009 | Liu et al. | | 370/338 |
| 2009/0204245 A1 | 8/2009 | Sustaeta | | 700/99 |
| 2009/0245286 A1 | 10/2009 | Kore et al. | | 370/475 |
| 2009/0268674 A1 | 10/2009 | Liu et al. | | 370/329 |
| 2009/0281677 A1 | 11/2009 | Botich | | 700/295 |
| 2010/0014599 A1 | 1/2010 | Holm et al. | | 375/260 |
| 2010/0108567 A1 | 5/2010 | Medoff | | 208/49 |
| 2010/0125347 A1 | 5/2010 | Martin et al. | | 700/31 |
| 2010/0152900 A1 | 6/2010 | Gurciullo et al. | | |
| 2010/0158764 A1 | 6/2010 | Hedrick | | 422/134 |
| 2010/0230324 A1 | 9/2010 | Al-Alloush et al. | | 208/82 |
| 2010/0262900 A1 | 10/2010 | Romatier et al. | | 715/219 |
| 2011/0112659 A1 | 5/2011 | Pachner et al. | | 700/29 |

(56) References Cited

U.S. PATENT DOCUMENTS

| | | | |
|---|---|---|---|
| 2011/0152590 A1 | 6/2011 | Sadler et al. | 585/313 |
| 2011/0152591 A1 | 6/2011 | Sadler et al. | 585/313 |
| 2011/0311014 A1 | 12/2011 | Hottovy et al. | 376/283 |
| 2012/0029966 A1 | 2/2012 | Cheewakriengkrai et al. | 705/7.25 |
| 2012/0083933 A1 | 4/2012 | Subbu et al. | 700/291 |
| 2012/0095808 A1 | 4/2012 | Kattapuram et al. | 705/7.37 |
| 2012/0104295 A1 | 5/2012 | Do et al. | 251/129.01 |
| 2012/0121376 A1 | 5/2012 | Huis in Het Veld | 415/1 |
| 2012/0123583 A1 | 5/2012 | Hazen et al. | |
| 2012/0197616 A1 | 8/2012 | Trnka | 703/6 |
| 2012/0259583 A1 | 10/2012 | Noboa et al. | |
| 2013/0029587 A1 | 1/2013 | Gandhi et al. | 455/7 |
| 2013/0031960 A1 | 2/2013 | Delrahim | 73/40.5 R |
| 2013/0079899 A1 | 3/2013 | Baramov | 700/32 |
| 2013/0090088 A1 | 4/2013 | Chevsky et al. | 455/411 |
| 2013/0094422 A1 | 4/2013 | Thanikachalam | 370/312 |
| 2013/0172643 A1 | 7/2013 | Pradeep | 585/310 |
| 2013/0253898 A1 | 9/2013 | Meagher et al. | 703/18 |
| 2013/0270157 A1 | 10/2013 | Ferrara | 208/48 AA |
| 2013/0311437 A1 | 11/2013 | Stluka et al. | 707/706 |
| 2013/0327052 A1 | 12/2013 | O'Neill | 60/772 |
| 2014/0008035 A1 | 1/2014 | Patankar et al. | |
| 2014/0026598 A1 | 1/2014 | Trawicki | 62/56 |
| 2014/0074273 A1 | 3/2014 | Mohideen et al. | 700/98 |
| 2014/0114039 A1 | 4/2014 | Benham et al. | 526/348.5 |
| 2014/0131027 A1 | 5/2014 | Chir | 165/300 |
| 2014/0163275 A1 | 6/2014 | Yanagawa et al. | 585/319 |
| 2014/0179968 A1 | 6/2014 | Yanagawa et al. | 585/476 |
| 2014/0212978 A1 | 7/2014 | Sharpe, Jr. et al. | 436/6 |
| 2014/0294683 A1 | 10/2014 | Siedler | 422/129 |
| 2014/0294684 A1 | 10/2014 | Siedler | 422/129 |
| 2014/0296058 A1 | 10/2014 | Sechrist et al. | 502/53 |
| 2014/0309756 A1 | 10/2014 | Trygstad | 700/31 |
| 2014/0337256 A1 | 11/2014 | Varadi et al. | 706/12 |
| 2014/0337277 A1 | 11/2014 | Asenjo et al. | |
| 2015/0059714 A1 | 3/2015 | Bernards | 123/568.11 |
| 2015/0060331 A1 | 3/2015 | Sechrist et al. | |
| 2015/0077263 A1 | 3/2015 | Ali et al. | 340/679 |
| 2015/0078970 A1 | 3/2015 | Iddir et al. | 422/218 |
| 2015/0098862 A1 | 4/2015 | Lok et al. | 422/49 |
| 2015/0158789 A1 | 6/2015 | Keusenkothen | |
| 2015/0185716 A1 | 7/2015 | Wichmann et al. | 700/287 |
| 2015/0276208 A1 | 10/2015 | Maturana et al. | 700/274 |
| 2015/0284641 A1 | 10/2015 | Shi | 208/113 |
| 2015/0330571 A1 | 11/2015 | Beuneken | 141/4 |
| 2016/0033941 A1 | 2/2016 | T et al. | 700/81 |
| 2016/0048119 A1 | 2/2016 | Wojsznis | 700/11 |
| 2016/0098037 A1 | 4/2016 | Zornio et al. | 700/20 |
| 2016/0098234 A1 | 4/2016 | Weaver | 358/1.15 |
| 2016/0122663 A1 | 5/2016 | Pintart et al. | |
| 2016/0147204 A1 | 5/2016 | Wichmann et al. | 700/287 |
| 2016/0237910 A1 | 8/2016 | Saito | |
| 2016/0260041 A1 | 9/2016 | Horn et al. | |
| 2016/0291584 A1 | 10/2016 | Horn et al. | |
| 2016/0292188 A1 | 10/2016 | Horn et al. | |
| 2016/0292325 A1 | 10/2016 | Horn et al. | |
| 2016/0313653 A1 | 10/2016 | Mink | |
| 2016/0363315 A1 | 12/2016 | Colannino et al. | |
| 2017/0009932 A1 | 1/2017 | Oh | |
| 2017/0058213 A1 | 3/2017 | Oprins | 585/303 |
| 2017/0082320 A1 | 3/2017 | Wang | |
| 2017/0107188 A1 | 4/2017 | Kawaguchi | |
| 2017/0284410 A1 | 10/2017 | Sharpe, Jr. | |
| 2017/0315543 A1 | 11/2017 | Horn et al. | |
| 2017/0323038 A1 | 11/2017 | Horn et al. | |
| 2017/0352899 A1 | 12/2017 | Asai | |
| 2018/0046155 A1 | 2/2018 | Horn et al. | |
| 2018/0081344 A1 | 3/2018 | Romatier et al. | |
| 2018/0082569 A1 | 3/2018 | Horn et al. | |
| 2018/0121581 A1 | 5/2018 | Horn et al. | |
| 2018/0122021 A1 | 5/2018 | Horn et al. | |
| 2018/0155638 A1 | 6/2018 | Al-Ghamdi et al. | 208/79 |
| 2018/0155642 A1 | 6/2018 | Al-Ghamdi et al. | |
| 2018/0197350 A1 | 7/2018 | Kim | |
| 2018/0275690 A1 | 9/2018 | Lattanzio et al. | |
| 2018/0275691 A1 | 9/2018 | Lattanzio et al. | |
| 2018/0275692 A1 | 9/2018 | Lattanzio et al. | |
| 2018/0280914 A1 | 10/2018 | Victor et al. | |
| 2018/0280917 A1 | 10/2018 | Victor et al. | |
| 2018/0282633 A1 | 10/2018 | Van de Cotte et al. | |
| 2018/0282634 A1 | 10/2018 | Van de Cotte et al. | |
| 2018/0282635 A1 | 10/2018 | Van de Cotte et al. | |
| 2018/0283368 A1 | 10/2018 | Van de Cotte et al. | |
| 2018/0283392 A1 | 10/2018 | Van de Cotte et al. | |
| 2018/0283404 A1 | 10/2018 | Van de Cotte et al. | |
| 2018/0283811 A1 | 10/2018 | Victor et al. | |
| 2018/0283812 A1 | 10/2018 | Victor et al. | |
| 2018/0283813 A1 | 10/2018 | Victor et al. | |
| 2018/0283815 A1 | 10/2018 | Victor et al. | |
| 2018/0283816 A1 | 10/2018 | Victor et al. | |
| 2018/0283818 A1 | 10/2018 | Victor et al. | |
| 2018/0284705 A1 | 10/2018 | Van de Cotte et al. | |
| 2018/0286141 A1 | 10/2018 | Van de Cotte et al. | |
| 2018/0311609 A1 | 11/2018 | McCool et al. | |
| 2018/0362862 A1 | 12/2018 | Gellaboina et al. | |
| 2018/0363914 A1 | 12/2018 | Faiella et al. | |
| 2018/0364747 A1 | 12/2018 | Charr et al. | |
| 2019/0002318 A1 | 1/2019 | Thakkar et al. | |
| 2019/0003978 A1 | 1/2019 | Shi et al. | |
| 2019/0015806 A1 | 1/2019 | Gellaboina et al. | |
| 2019/0041813 A1 | 2/2019 | Horn et al. | |
| 2019/0083920 A1 | 3/2019 | Bjorklund et al. | |
| 2019/0101336 A1 | 4/2019 | Victor et al. | |
| 2019/0101342 A1 | 4/2019 | Victor et al. | |
| 2019/0101907 A1 | 4/2019 | Charr et al. | |
| 2019/0102966 A1 | 4/2019 | Lorenz | |
| 2019/0108454 A1 | 4/2019 | Banerjee et al. | |
| 2019/0120810 A1 | 4/2019 | Kumar et al. | |
| 2019/0151814 A1 | 5/2019 | Victor et al. | |
| 2019/0155259 A1 | 5/2019 | Romatier et al. | |

FOREIGN PATENT DOCUMENTS

| | | | | |
|---|---|---|---|---|
| EP | | 2801937 A1 | 11/2014 | G06Q 10/06 |
| GB | | 1134439 A | 11/1968 | G01N 31/22 |
| WO | WO | 1990/010083 A1 | 9/1990 | C12Q 1/04 |
| WO | WO | 2001/060951 A1 | 8/2001 | C10G 51/04 |
| WO | WO | 2006/044408 A1 | 4/2006 | F23D 14/72 |
| WO | WO | 2007/095585 A2 | 8/2007 | A61K 31/721 |
| WO | WO | 2009/046095 A1 | 4/2009 | G06F 11/00 |
| WO | WO | 2014/042508 A1 | 3/2014 | G06Q 50/04 |
| WO | WO | 2014/123993 A1 | 8/2014 | G06F 17/00 |
| WO | WO | 2016/141128 A1 | 9/2016 | G06Q 10/06 |
| WO | WO | 2017/079058 A1 | 5/2017 | B01D 1/14 |

OTHER PUBLICATIONS

Bespalov A. V. et al., Control systems of chemical and technological processes, pp. 508-509 (2001) (Russian).

Daniel Goebel, Dry Gas Seal Contamination During Operation and Pressurization Hold, [online], Feb. 2016, [retrieved on Jun. 19, 2019], Retrieved from <https://core.ac.uk/download/pdf/84815277.pdf> (Year: 2016).

EnergyMEDOR®, Product brochure (Nov. 2014).

Chistof Huber, Density and Concentration Measurement Application for Novel MEMS-based Micro Densitometer for Gas, [online], 2016, [retrieved on Jun. 19, 2019]. Retrieved from <https://www.ama-science.org/proceedings/getFile/ZwZ1 BD==> (Year: 2016).

Loiters, Real-time Composition Determination of Gas Mixtures, [online], 2015, [retrieved on Jun. 19, 2019], Retrieved from <https://www.ama-science.org/proceedings/getFile/ZwNOZj==> (Year: 2015).

Maybeck, Peter S., "Stochastic models, estimation, and control," vol. 1, Academic Press (1979), 19 pages.

Jan. 17, 2019—(WO) International Search Report and Written Opinion—App No. PCT/US2018/053945.

\* cited by examiner

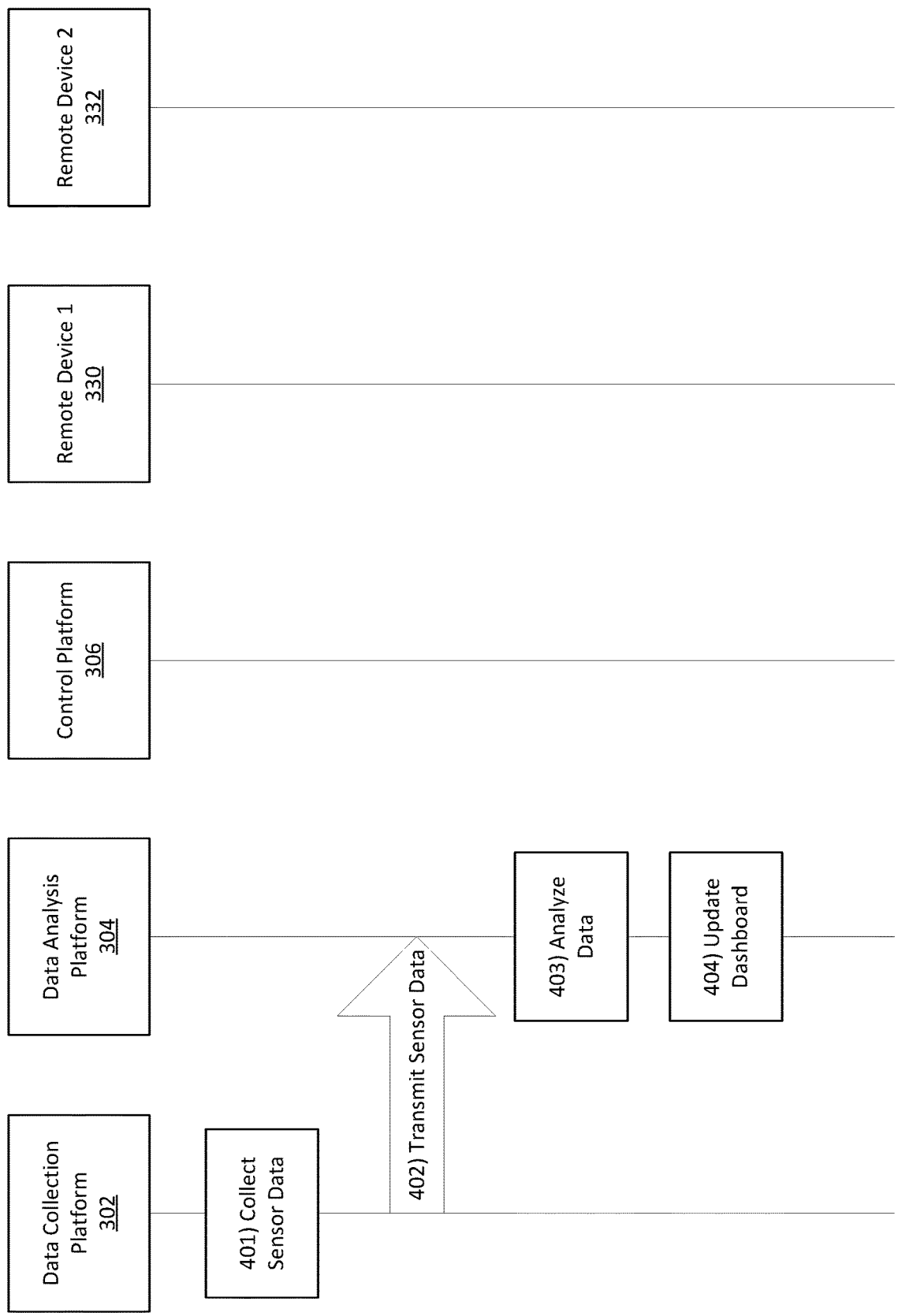

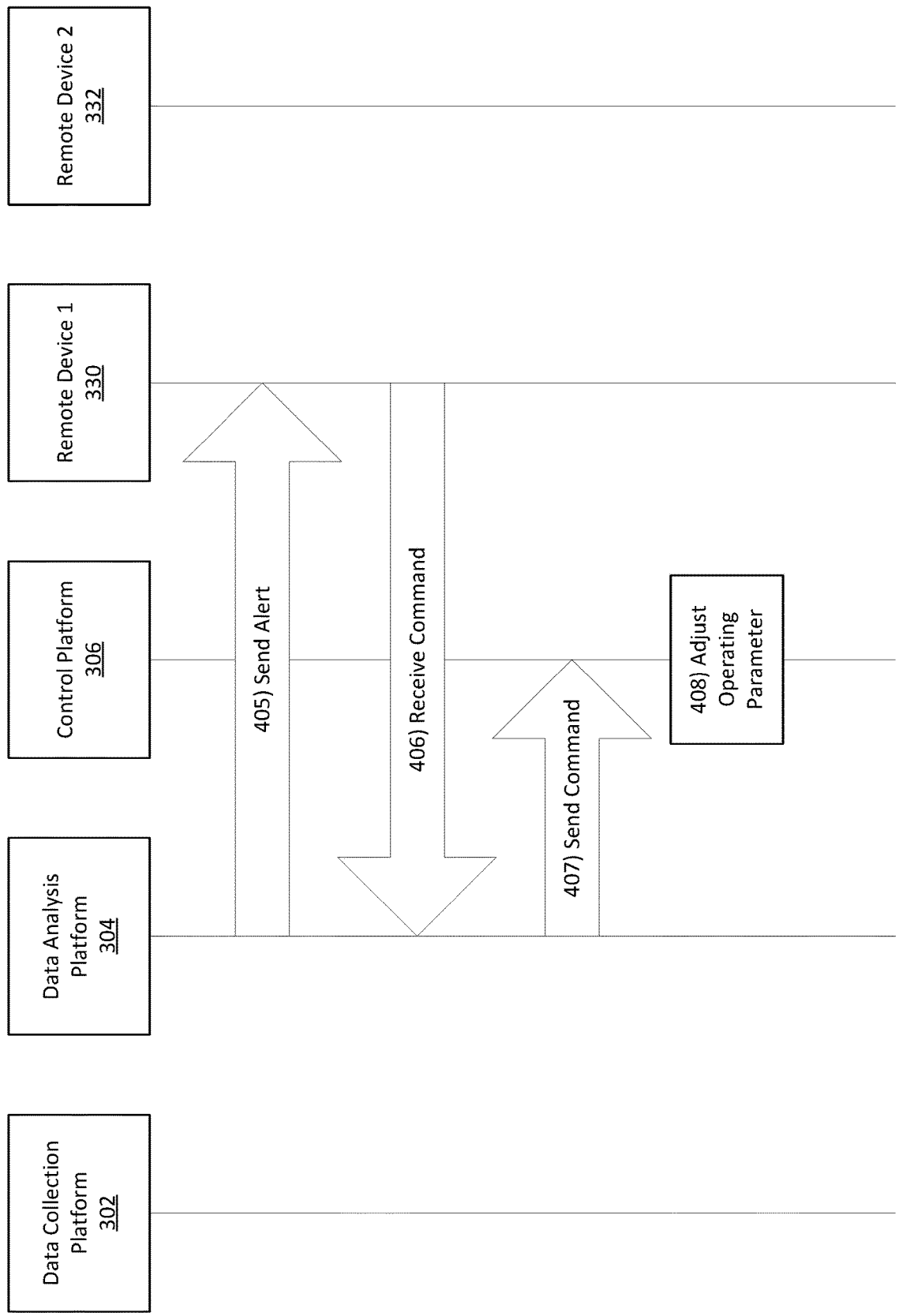

REMOTE MONITORING OF CHLORIDE TREATERS USING A PROCESS SIMULATOR BASED CHLORIDE DISTRIBUTION ESTIMATE

CROSS-REFERENCE TO RELATED APPLICATION

This application claims the benefit of priority under 35 U.S.C. § 119(e) to U.S. Provisional Application No. 62/566,736, filed Oct. 2, 2017, which is incorporated by reference.

FIELD

The disclosure relates generally to a method and system for managing the operation of a plant, such as a chemical plant or a petrochemical plant or a refinery, and more particularly to a method for improving the performance of components that make up operations in a plant.

BACKGROUND

Industrial processes are typically implemented using large numbers of devices, such as pumps, valves, compressors, or other industrial equipment used to implement various aspects of the industrial processes. With these large numbers of devices, scheduled or responsive maintenance needs to be efficient in order to maintain overall efficiency of a plant.

SUMMARY

The following summary presents a simplified summary of certain features. The summary is not an extensive overview and is not intended to identify key or critical elements.

One or more embodiments may include a system comprising one or more sensors configured to measure operating information for a chloride treater, a data collection platform, a data analysis platform, and/or a control platform. The data collection platform may include one or more processors of the data collection platform; and memory storing executable instructions that, when executed, cause the data collection platform to: receive sensor data from the one or more sensors; correlate the sensor data with metadata comprising time data; and transmit the sensor data. The data analysis platform may include one or more processors of the data analysis platform; and memory storing executable instructions that, when executed, cause the data analysis platform to: receive the sensor data from the data collection platform; analyze the sensor data; transmit the sensor data and calculations to a dashboard; and based on the analyzed sensor data, transmit a command for an adjustment to an operating condition related to the chloride treater. The control platform may include one or more processors of the control platform; and memory storing executable instructions that, when executed, cause the control platform to: receive the command for the adjustment to the operating condition related to the chloride treater; and adjust an element of the chloride treater based on the command for the adjustment to the operating condition related to the chloride treater.

One or more embodiments may include a method comprising: receiving, by a data analysis computing device, sensor data for a sensor associated with a chloride treater; based on analyzing the sensor data, determining a current operating condition for an element of the chloride treater; determining a difference between the current operating condition for the element of the chloride treater and a design operating condition for the element of the chloride treater; based on the analyzed sensor data, determining a recommended adjustment to the element of the chloride treater to reduce the difference between the current operating condition and the design operating condition; and displaying the difference between the current operating condition and the design operating condition on a dashboard.

One or more embodiments may include Non-transitory computer-readable media storing executable instructions that, when executed by one or more processors, cause a system to: receive sensor data from one or more sensors configured to measure operating information for a chloride treater; correlate the sensor data with metadata comprising time data; analyze the sensor data; generate a dashboard based on the sensor data and calculations about the sensor data; based on the analyzed sensor data, display information about the chloride treater; and based on the analyzed sensor data, send an alert about the chloride treater.

Other technical features may be readily apparent to one skilled in the art from the following figures, descriptions, and claims.

BRIEF DESCRIPTION OF DRAWINGS

The present disclosure is illustrated by way of example and not limited in the accompanying figures in which like reference numerals indicate similar elements and in which:

FIGS. 4A-4B depict an illustrative flow diagram of one or more steps that one or more devices may perform in controlling one or more aspects of a plant operation in accordance with one or more example embodiments;

DETAILED DESCRIPTION

In the following description of various illustrative embodiments, reference is made to the accompanying drawings, which form a part hereof, and in which is shown, by way of illustration, various embodiments in which aspects of the disclosure may be practiced. It is to be understood that other embodiments may be used, and structural and functional modifications may be made, without departing from the scope of the present disclosure.

It is noted that various connections between elements are discussed in the following description. It is noted that these connections are general and, unless specified otherwise, may be direct or indirect, wired or wireless, and that the specification is not intended to be limiting in this respect.

A chemical plant or a petrochemical plant or a refinery may include one or more pieces of equipment that process one or more input chemicals to create one or more products, for example conversion of petroleum refinery naphthas distilled from crude oil into high-octane liquid products. References herein to a "plant" are to be understood to refer to any of various types of chemical and petrochemical manufacturing or refining facilities. References herein to a plant "operators" are to be understood to refer to and/or include, without limitation, plant planners, managers, engineers, technicians, technical advisors, specialists (e.g., in instrumentation, pipe fitting, and welding), shift personnel, and others interested in, starting up, overseeing, monitoring operations of, and shutting down, the plant.

Figure 1:
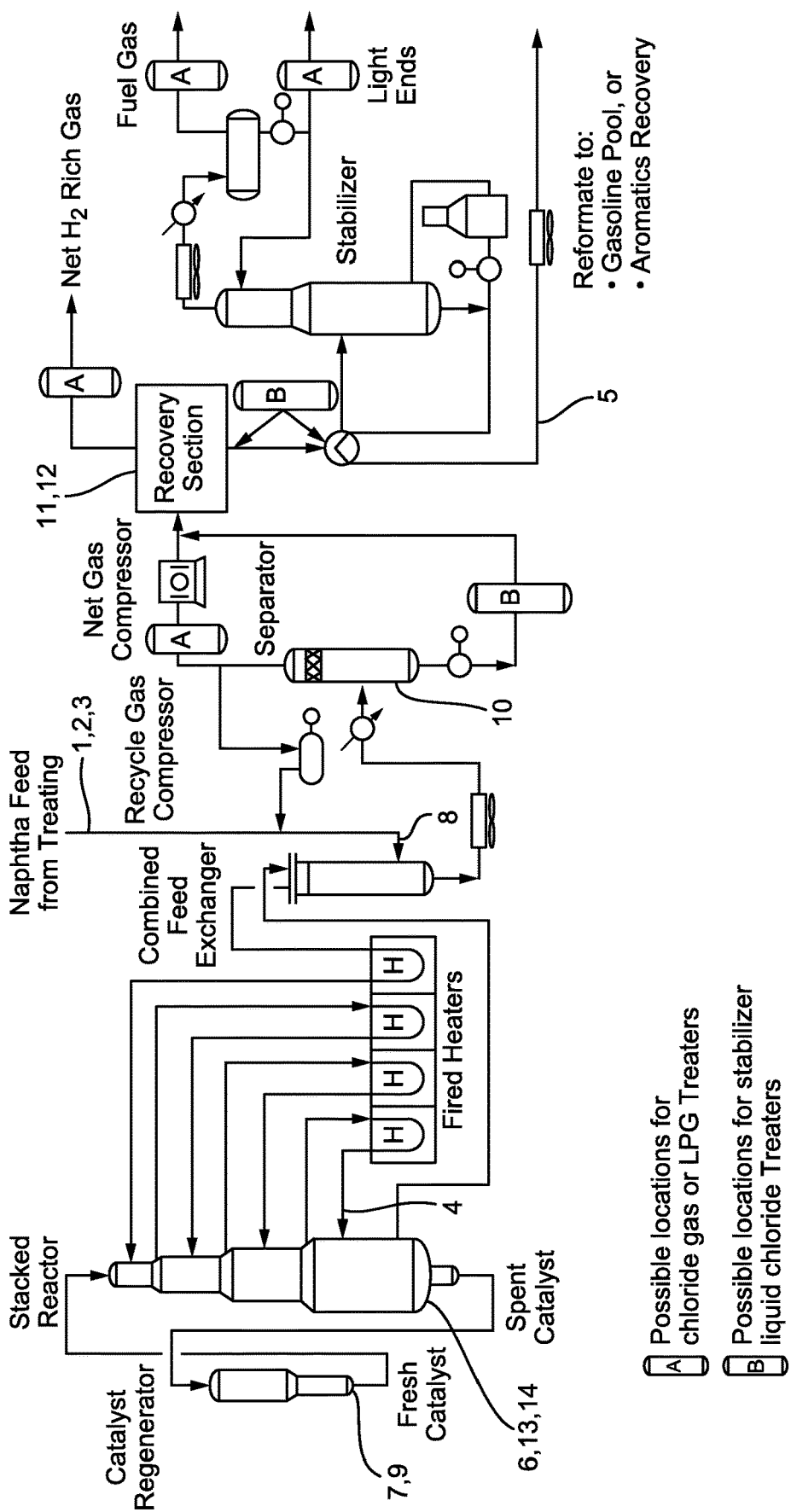
FIG. 1 depicts an illustrative catalytic reforming process having chloride treaters in accordance with one or more example embodiments.

As shown in FIG. 1, catalytic reforming converts petroleum refinery naphthas distilled from crude oil into high-octane liquid products called reformates. In particular, the process converts low-octane linear hydrocarbons (paraffins) into branched alkanes (isoparaffins) and cyclic naphthenes, which are then partially dehydrogenated to produce high-octane aromatic hydrocarbons. The dehydrogenation also produces significant amounts of byproduct hydrogen gas, which is fed into other refinery processes such as hydrocracking. A side reaction is hydrogenolysis, which produces light hydrocarbons of lower value, such as methane, ethane, propane and butanes.

Reformate is used for gasoline blending stock and is the main source of aromatic bulk chemicals such as benzene, toluene, xylene, and ethylbenzene, which may be used, for example, as raw materials for conversion into plastics.

Catalysts used for catalytic reforming are treated with organic chloride to condition the catalysts. This treatment leads to chloride compounds (e.g., hydrogen chloride (HCl) and various organic chlorides) in the reactor effluent (product streams) at low ppm levels. Such compounds are often referred to as trace chloride contaminants. If untreated, these chlorides can cause problems, such as formation and deposition of ammonium chloride, chloride related corrosion (e.g., corrosion of austenitic stainless steels and downstream piping/equipment), poisoning of downstream catalysts, and other effects. Accordingly, product recovery in typical catalytic dehydrogenation processes may include a process for removal of chloride contaminants.

Chloride treaters may be located in the product streams to remove the chloride contaminants. Such treaters use adsorbents and may be used to remove chloride from both gas and liquid streams, as illustrated in FIG. 1. One or a series of chloride treaters may be used. For example, a series of first chloride treaters remove most chloride, and second and third chloride treaters may be used to remove remaining chloride.

The adsorbent may be selected based on the particular process. The adsorbent bed may be a fixed bed or a fluidized bed. The adsorbent may be non-regenerative or regenerative. Typically, non-regenerative fixed bed adsorbent units are used. The level of removal of inorganic and organic chloride can vary depending on the chloride source, among other factors. As examples, suitable adsorbents may include, but are not limited to, Na doped alumina, molecular sieve, or zinc oxide. The expected life of the adsorbent material used may be continuously affected by operational conditions of the entire process, equipment such as the reactor, and the chloride treater itself.

Many plant operators perform little to no past/present/future analysis on the unit operation to determine the best chloride treater utilization and/or expected life cycle. Instead, samples are taken downstream of the chloride treater to see if the adsorbent is still actively adsorbing the chloride. By the time the samples indicate that unacceptable levels of chloride are exiting the treater, the downstream equipment has already been exposed to the corrosive chloride. Then the treater would be taken offline to reload (or regenerate) the adsorbent. It would be better to be proactive than reactive and reload the adsorbent before release of chloride compounds downstream. But one would not want to replace the adsorbent too early, as the adsorbent is expensive and taking a treater offline could be expensive and time consuming.

Monitoring Chloride Treaters

The continuous catalyst reforming process, including the catalyst reformer unit and chloride treaters, may be monitored in order to predict when adsorbent replacement or regeneration is needed. For example, one or more sensors and measurement devices may be used to monitor certain conditions or parameters. A system may be configured to take one or more actions, such as sending one or more alerts or sounding one or more alarms if certain conditions are met.

Sensors used to gather information that is used to determine such indicators may include, for example, temperature sensors, pressure sensors, flow sensors, moisture sensors/analyzers, infrared cameras, tunable laser diodes, chemical sensors/analyzers, and/or gas valve position sensors. Examples of measurements that may be taken during the catalytic reforming process may include flow, temperature, pressure, and/or analytical measurements.

Referring again to FIG. 1, gas chloride treaters are indicated by A and liquid chloride treaters are indicated by B. Analytic measurements are taken in various spots in the process as indicated by the numbers. For example, numbers 1, 2, and 3 relate to measurements taken where naphtha is fed into the process. Measurements may be taken at other areas, as indicated in table 500 of FIG. 5. For example, illustrative measurements taken may relate to the reactor, feed, product flow, and/or compositions. Some measurements may be determined based on information gathered by one or more sensors, while some measurements may be determined based on laboratory analysis. Although additional measurements may be taken of the chloride treaters, for the purposes of predicting the life cycle of an adsorbent bed, it is important to determine the amount of the chloride contaminants in the various streams. Properties of the absorbent may also be necessary to determine what percentage of the treater capacity has been spent and how much capacity is left.

Figure 2:
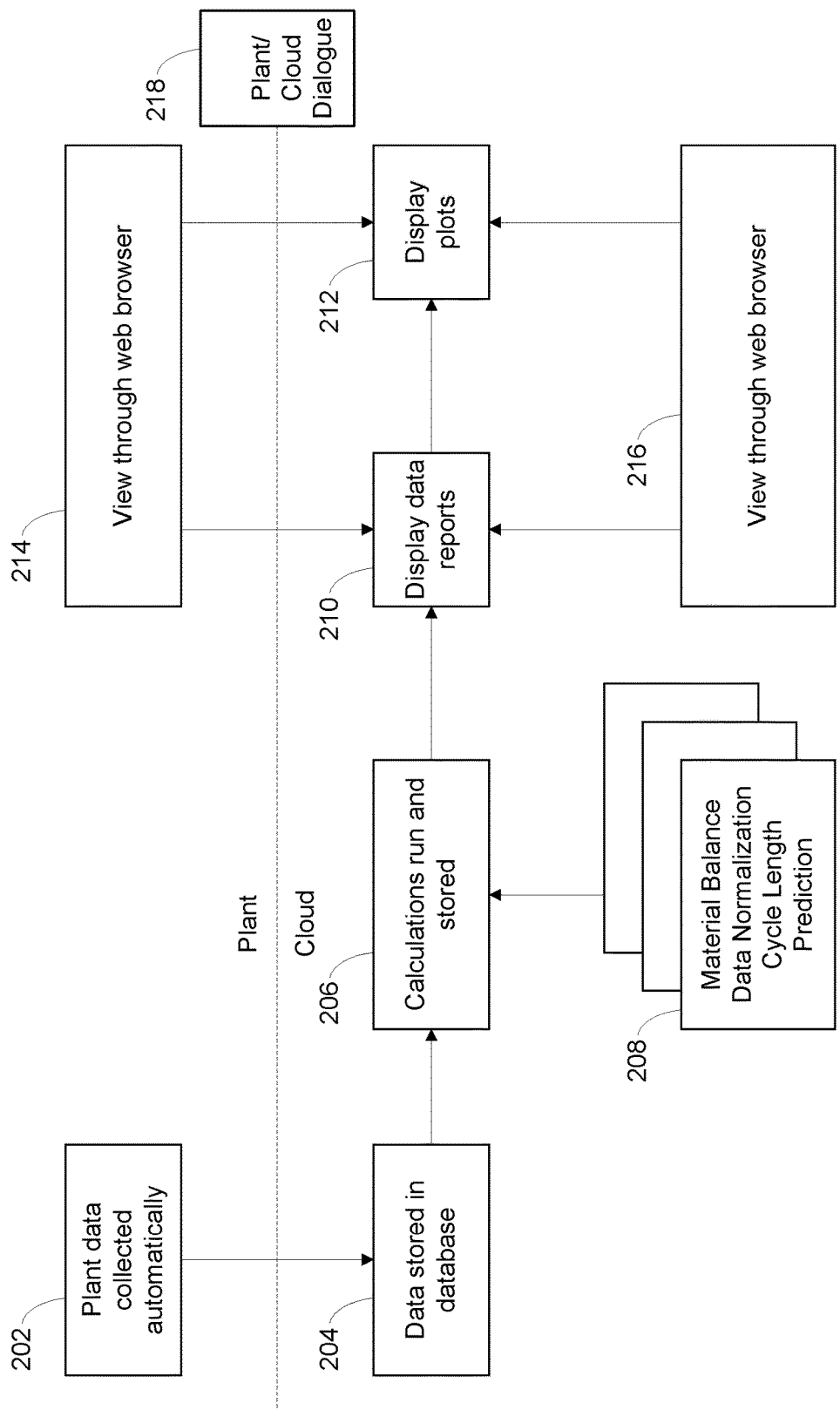
FIG. 2 depicts a flow chart of data collection and processing in accordance with one or more example embodiments.
Figure 5:
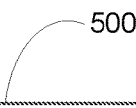
FIG. 5 depicts a table of illustrative measurements related to one or more aspects of a plant operation in accordance with one or more example embodiments.

As seen in FIG. 2, plant data may be collected automatically (202) from the various sensor data and measurements sites, such as indicated in table 500 of FIG. 5, and the collected data may be transmitted to a cloud-computing system via a plant-cloud dialogue (218). The data may be stored (204) in a database. Process know-how and adsorbent application knowledge may be incorporated into the data and analytics. Calculations (206) may be performed including, e.g., material balance, data normalization, and/or cycle length prediction (208). For example, the system may use various algorithms and simulations to proactively determine adsorbent bed operation status and utilization rate. The collected plant data may be used as input for the simulation so predictions are based on current operational conditions. For example, the amount of chloride accumulated on each treater may be used to determine the current chloride treater utilization percentage and predict the expected end of life. Using a process simulation, the system may calculate the rate at which chlorides are lost from the catalyst in the reformer reactor and/or how chlorides are distributed in the reformer products.

Data reports (210) and plots (212) may be displayed including advance notice of the expected reload date. The data may be displayed via a web site (214, 216) provided to one or more devices that are accessible to the plant operators and/or other technicians and experts. The web site may be accessible from within the plant and/or from outside the plant. In some embodiments, one or more portions of the web site may be accessible only from inside the plant, while one or more other portions of the web site may be accessible only from outside the plant. The system may provide information regarding operational issues related to chlorides breakthrough, improve the reliability of chloride treating and downstream process protection, and provide a planning date for the chloride treater reload.

As time advances, real plant data can be reviewed and more accurate fault models based on catalyst/adsorbent materials can be developed. Ultimately, a more robust product tailored for a specific plant can be developed.

Therefore, aspects of the system described herein are directed to monitoring and analysis of utility process conditions and interrelationships (e.g., reactants, chloride, catalyst, adsorbent). The system may further provide data, alerts, and/or automated or manual responses to data, which may allow for corrective actions to avoid unscheduled shutdowns associated with poor performance, e.g., poor adsorption resulting in corrosion.

Aspects of the disclosure may be used to identify deteriorating equipment. There may or may not be anything that can be done to correct issues or problems associated with the issues in existing equipment, depending on the cause of the issues. In some aspects, process changes or operating conditions may be altered to preserve the equipment until the next scheduled maintenance period.

Sensor Data Collection and Processing

The present disclosure is directed to a system of improving chloride treater efficiencies on an ongoing and consistent basis, and delivering timely and/or regular reports indicating current performance. The present disclosure is further directed to a system that may interpret data and/or generate recommendations regarding what actions may be performed to improve chloride treater performance. These actions may include modifications to reactor, process flow, and/or chloride treater conditions.

The present disclosure provides an alternative to a rudimentary data collection and analysis process, which may yield poor recommendations that are not generated with the required expertise and/or are not provided in a timely manner. The present disclosure provides improved reporting and recommendations via a software monitoring system that delivers a timely report (e.g., web based), and/or additional recommendations, alerts, or triggers of remedial or corrective actions.

The system may rely on sensing or measuring various parameters including measurement of flow concentrations into and out of the catalytic reactor, for example, and temperature, pressure, and other performance characteristics to predict reaction kinetics. Input may also include the type of chloride treater, whether there is a gaseous or liquid stream, the type of adsorbent, and the adsorbent's adsorption characteristics. The input and data is used to predict the amount of chloride entering the chloride treaters (e.g., per hour, per day, per week) and end of life of the chloride treater.

One or more automated algorithms may be used to minimize the need for operators to review data. In particular, a reforming chemistry kinetic model may be embedded into a process simulation including key vapor-liquid equilibria calculations. This establishes key process variables that can be confirmed against data collected at the facility to describe the conditions influencing the catalyst and process streams. A surface equilibrium model may be applied to describe how the catalyst and process streams influence the chloride loss from the catalyst within the reactors, as well as how catalysts age during plant operation. A reaction mechanism may describe the formation of organic chlorides within the process reactors.

A dashboard (e.g., dashboard 305, dashboard 313) may be used to present the data and predict how much chloride is in the process streams in order to predict the life of an adsorbent bed. The dashboard may present current utilization percentage of the treater. The dashboard may include plots, tables, animated shapes, or the like in a web site, mobile app, desktop application, dedicated platform, or the like.

Figure 3A:
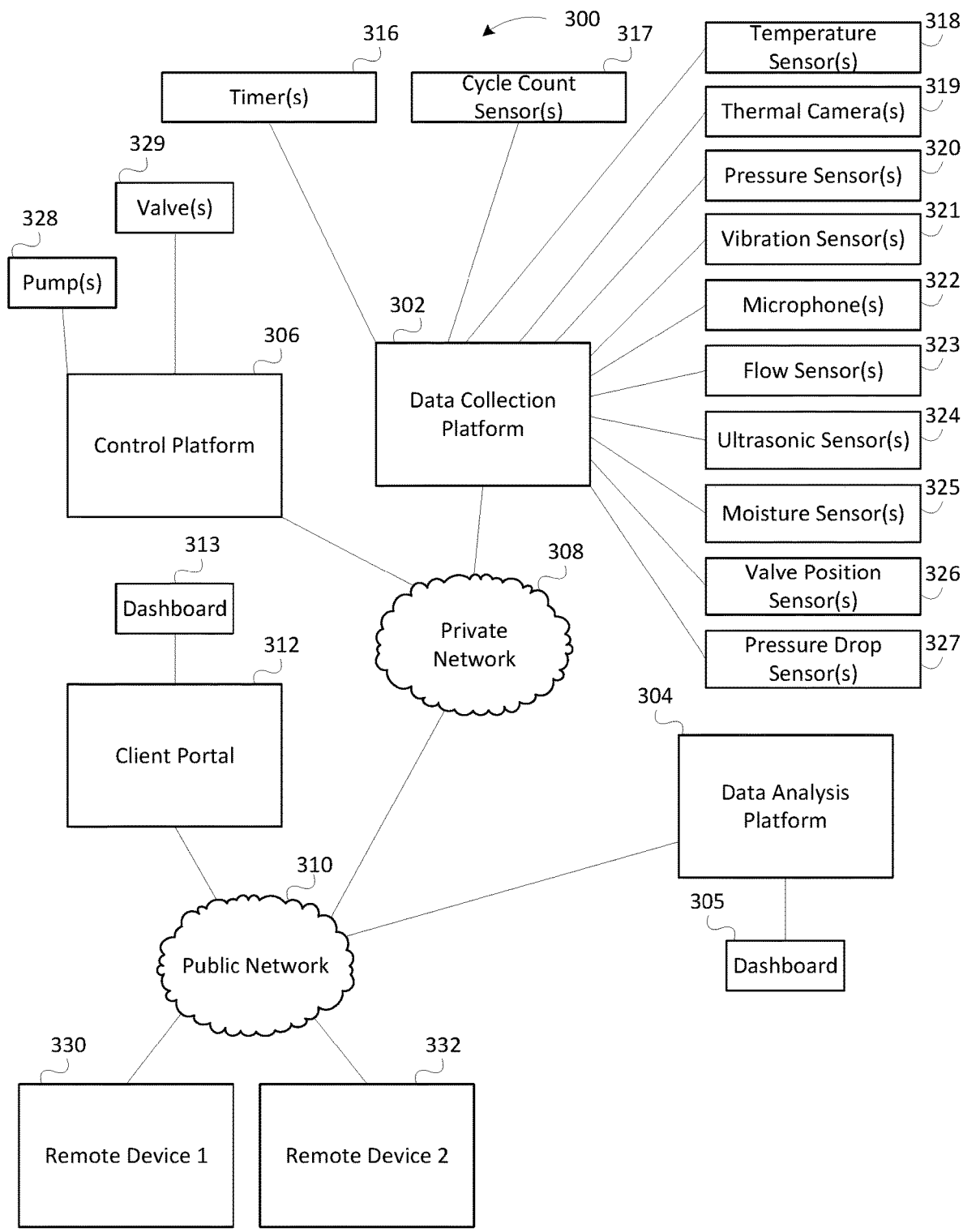
FIG. 3A depicts an illustrative computing environment for managing the operation of one or more pieces of equipment in a plant in accordance with one or more example embodiments.

The system may include one or more computing devices or platforms for collecting, storing, processing, and analyzing data from one or more sensors. FIG. 3A depicts an illustrative computing system that may be implemented at one or more components, pieces of equipment (e.g., reactors, chloride treaters), and/or plants. FIG. 3A-FIG. 3E (hereinafter collectively "FIG. 3"), show, by way of illustration, various components of the illustrative computing system in which aspects of the disclosure may be practiced. Other components may be used, and structural and functional modifications may be made, in one or more other embodiments without departing from the scope of the present disclosure. Moreover, various connections between elements are discussed in the following description, and these connections are general and, unless specified otherwise, may be direct or indirect, wired or wireless, and/or combination thereof, and that the specification is not intended to be limiting in this respect.

FIG. 3A depicts an illustrative operating environment 300 in which various aspects of the present disclosure may be implemented in accordance with example embodiments. The computing system environment 300 illustrated in FIG. 3A is only one example of a suitable computing environment and is not intended to suggest any limitation as to the scope of use or functionality contained in the disclosure. The computing system environment 300 may include various sensor, measurement, and data capture systems, a data collection platform 302, a data analysis platform 304, a control platform 306, a client portal 312, one or more networks, one or more remote devices, and/or one or more other elements. The numerous elements of the computing system environment 300 of FIG. 3A may be communicatively coupled through one or more networks. For example, the numerous platforms, devices, sensors, and/or components of the computing system environment may be communicatively coupled through a private network 308. The sensors may be positioned on various components in the plant and may communicate wirelessly or wired with one or more platforms illustrated in FIG. 3A. The private network 308 may comprise, in some examples, a network firewall device to prevent unauthorized access to the data and devices on the private network 308. Alternatively, the private network 308 may be isolated from external access through physical means, such as a hard-wired network with no external, direct-access point. The data communicated on the private network 308 may be optionally encrypted for further security. Depending on the frequency of collection and transmission of sensor measurements and other data to the data collection platform 302, the private network 308 may experience large bandwidth usage and be technologically designed and arranged to accommodate for such technological issues. Moreover, the computing system environment 300 may also include a public network 310 that may be accessible to remote devices (e.g., remote device 330, remote device 332). In some examples, the remote device may be located not in the proximity (e.g., more than one mile away) of the various sensor, measurement, and data capture systems illustrated in FIG. 3A. In other examples, the remote device may be physically located inside a plant, but restricted from access to the private network 308; in other words, the adjective "remote," need not necessarily require the device to be located at a great distance from the sensor systems and other components.

Although the computing system environment 300 of FIG. 3A illustrates logical block diagrams of numerous platforms and devices, the disclosure is not so limited. In particular, one or more of the logical boxes in FIG. 3 may be combined into a single logical box or the functionality performed by a single logical box may be divided across multiple existing or new logical boxes. For example, aspects of the functionality performed by the data collection platform 302 may be incorporated into one or each of the sensor devices illustrated in FIG. 3A. As such, the data collection may occur local to the sensor device, and the enhanced sensor system may communicate directly with one or more of the control platform 306 and/or data analysis platform 304. Such an embodiment is contemplated by FIG. 3A. Moreover, in such an embodiment, the enhanced sensor system may measure values common to a sensor, but may also filter the measurements such just those values that are statistically relevant or of-interest to the computing system environment are transmitted by the enhanced sensor system. As a result, the enhanced sensor system may include a processor (or other circuitry that enables execution of computer instructions) and a memory to store those instructions and/or filtered data values. The processor may be embodied as an application-specific integrated circuit (ASIC), FPGA, or other hardware- or software-based module for execution of instructions. In another example, one or more sensors illustrated in FIG. 3A may be combined into an enhanced, multi-purpose sensor system. Such a combined sensor system may provide economies of scale with respect to hardware components such as processors, memories, communication interfaces, and others.

In yet another example, the data collection platform 302 and data analysis platform 304 may reside on a single server computer or virtual machine and be depicted as a single, combined logical box on a system diagram. Moreover, a data store may be illustrated in FIG. 3A separate and apart from the data collection platform 302 and data analysis platform 304 to store a large amount of values collected from sensors and other components. The data store may be embodied in a database format and may be made accessible to the public network 310; meanwhile, the control platform 306, data collection platform 302, and data analysis platform 304 may be restricted to the private network 308 and left inaccessible to the public network 310. As such, the data collected from a plant may be shared with users (e.g., engineers, data scientists, others), a company's employees, and even third parties (e.g., subscribers to the company's data feed) without compromising potential security requirements related to operation of a plant. The data store may be accessible to one or more users and/or remote devices over the public network 310.

Referring to FIG. 3A, process measurements from various sensor and monitoring devices may be used to monitor conditions in, around, and on process equipment (e.g., reactors, separators, chloride treaters). Such sensors may include, but are not limited to, pressure sensors 320, differential pressure sensors, pressure drop sensors 327, flow sensors 323, temperature sensors 318 including thermal cameras 319 and skin thermocouples, capacitance sensors, weight sensors, gas chromatographs, moisture sensors 325, ultrasonic sensors 324, position sensors (e.g., valve position sensors 326), timing sensors, vibration sensors 321, level sensors, liquid level (hydraulic fluid) sensors, timers 316, cycle count sensors 317, microphones 322, and other sensors commonly found in the refining and petrochemical industry. Further, process laboratory measurements may be taken using gas chromatographs, liquid chromatographs, distillation measurements, octane measurements, and other laboratory measurements. System operational measurements also can be taken to correlate the system operation to the reactor measurements.

In addition, sensors may include transmitters and deviation alarms. These sensors may be programmed to set off an alarm, which may be audible and/or visual.

Other sensors may transmit signals to a processor or a hub that collects the data and sends to a processor. For example, temperature and pressure measurements may be sent to a hub (e.g., data collection platform 302). In one or more embodiments, temperature sensors 318 may include thermocouples, fiber optic temperature measurement, thermal cameras 319, and/or infrared cameras. Skin thermocouples may be applied to a wall of a reactor or chloride treater. A shielded (insulated) tube skin thermocouple assembly may be used to obtain accurate measurements. One example of a thermocouple may be a removable XTRACTO-Pad. A thermocouple can be replaced without any additional welding. Clips and/or pads may be used for ease of replacement. Fiber Optic cable can be attached to a unit, line, or vessel to provide a complete profile of temperatures.

Furthermore, flow sensors 323 may be used in flow paths such as the inlet to the path, outlet from the path, or within the path. Flow may be determined by pressure-drop across a known resistance, such as by using pressure taps. Other types of flow sensors include, but are not limited to, ultrasonic, turbine meter, hot wire anemometer, vane meter, Kármián™, vortex sensor, membrane sensor (membrane has a thin film temperature sensor printed on the upstream side, and one on the downstream side), tracer, radiographic imaging (e.g., identify two-phase vs. single-phase region of channels), an orifice plate in front of or integral to each tube or channel, pitot tube, thermal conductivity flow meter, anemometer, internal pressure flow profile, and/or measure cross tracer (measuring when the flow crosses one plate and when the flow crosses another plate).

A gas chromatograph on the feed or product streams into and out of the reactor and the chloride treater can be used to speciate the various components to provide empirical data to be used in calculations.

Sensor data, process measurements, and/or calculations made using the sensor data or process measurements may be used to monitor and/or improve the performance of the equipment and parts making up the equipment, as discussed in further detail below. For example, sensor data may be used to detect that a desirable or an undesirable chemical reaction is taking place within a particular piece of equipment, and one or more actions may be taken to encourage or inhibit the chemical reaction. Chemical sensors may be used to detect the presence of one or more chemicals or components in the streams, such as corrosive species (HCl, organic chlorides), oxygen, hydrogen, and/or water (moisture). Chemical sensors may use gas chromatographs, liquid chromatographs, distillation measurements, and/or octane measurements. In another example, equipment information, such as wear, efficiency, production, state, or other condition information, may be gathered and determined based on sensor data.

Corrective action may be taken based on determining this equipment information. For example, if the equipment is showing signs of wear or failure, corrective actions may be taken, such as taking an inventory of parts to ensure replacement parts are available, ordering replacement parts, and/or calling in repair personnel to the site. Certain parts of equipment may be replaced immediately. Other parts may be safe to continue to use, but a monitoring schedule may be adjusted. Alternatively or additionally, one or more inputs or controls relating to a process may be adjusted as part of the corrective action. These and other details about the equipment, sensors, processing of sensor data, and actions taken based on sensor data are described in further detail below.

Monitoring the reaction process includes collecting data that can be correlated and used to predict behavior or problems in different chloride treater used in the same plant or in other plants and/or processes. Data collected from the various sensors (e.g., measurements such as flow, pressure drop, thermal performance) may be correlated with external data. Process changes or operating conditions may be able to be altered to preserve the equipment until the next scheduled maintenance period. Fluids may be monitored for corrosive contaminants and pH may be monitored in order to predict reaction chemistry. At a high level, sensor data collected (e.g., by the data collection platform) and data analysis (e.g., by the data analysis platform) may be used together, for example, for process simulation, equipment simulation, and/or other tasks. For example, sensor data may be used for process simulation and reconciliation of sensor data. The resulting, improved process simulation may provide a stream of physical properties that are used to calculate heat flow and the like. These calculations may lead to thermal and pressure drop performance prediction calculations for specific equipment, and comparisons of equipment predictions to observations from the operating data (e.g., predicted/expected outlet temperature and pressure vs. measured outlet temperature and pressure). This may be used for identification of one or issues that may eventually lead to a potential control changes and/or recommendations.

Systems Facilitating Sensor Data Collection

Sensor data may be collected by a data collection platform 302. The sensors may interface with the data collection platform 302 via wired or wireless transmissions. Sensor data (e.g., temperature data) may be collected continuously or at periodic intervals (e.g., every second, every five seconds, every ten seconds, every minute, every five minutes, every ten minutes, every hour, every two hours, every five hours, every twelve hours, every day, every other day, every week, every other week, every month, every other month, every six months, every year, or another interval). Data may be collected at different locations at different intervals. The data collection platform 302 may continuously or periodically (e.g., every second, every minute, every hour, every day, once a week, once a month) transmit collected sensor data to a data analysis platform 304, which may be nearby or remote from the data collection platform 302.

Figure 3B:
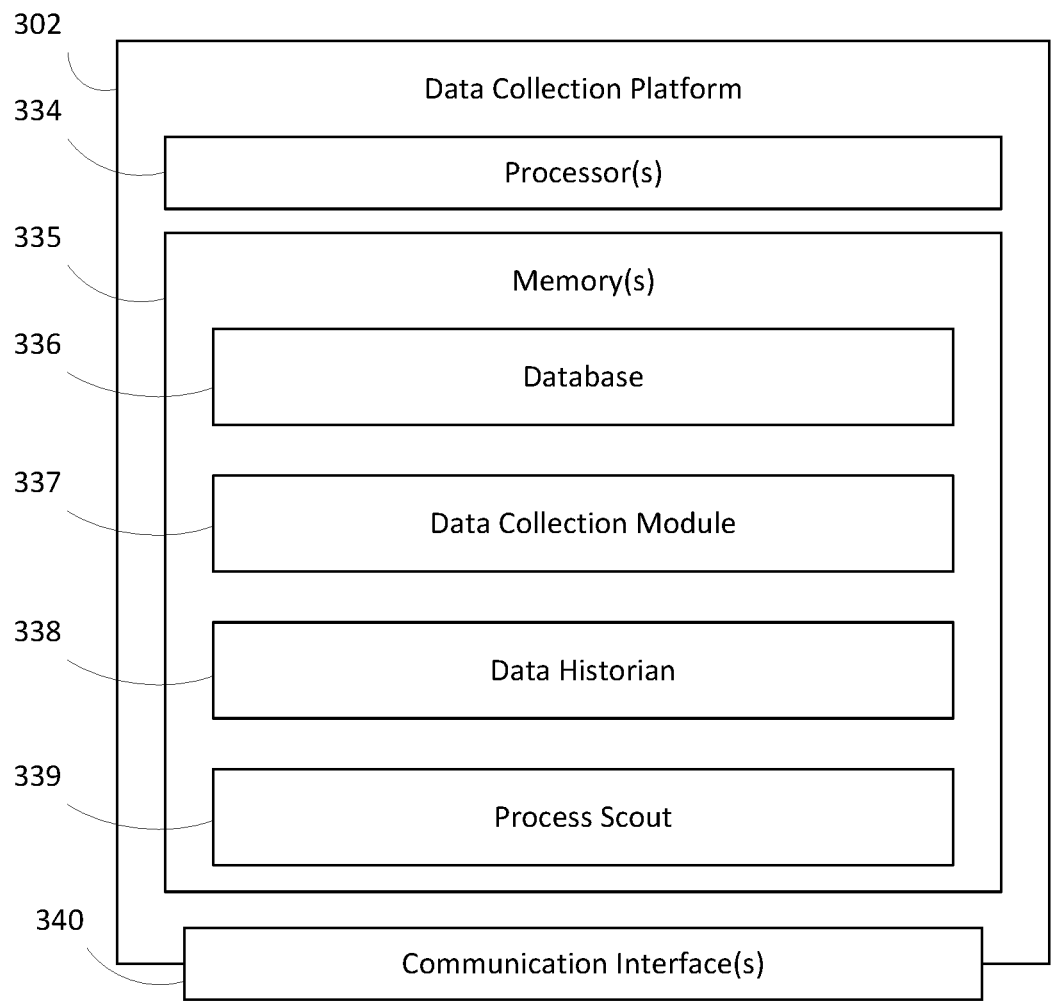
FIG. 3B depicts an illustrative data collection computing platform for collecting data related to the operation of one or more pieces of equipment in a plant in accordance with one or more example embodiments.
Figure 3C:
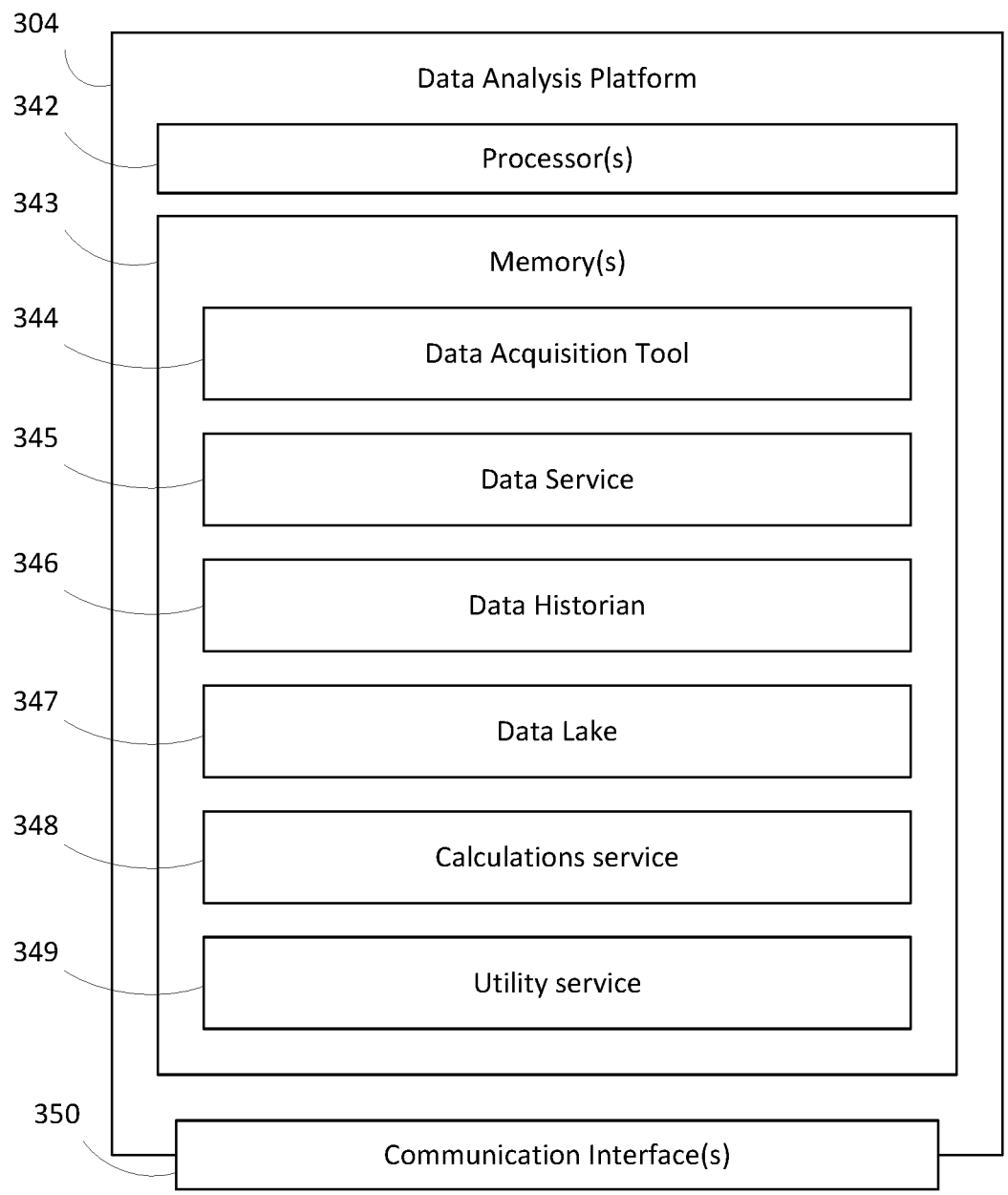
FIG. 3C depicts an illustrative data analysis computing platform for analyzing data related to the operation of one or more pieces of equipment in a plant in accordance with one or more example embodiments.
Figure 3D:
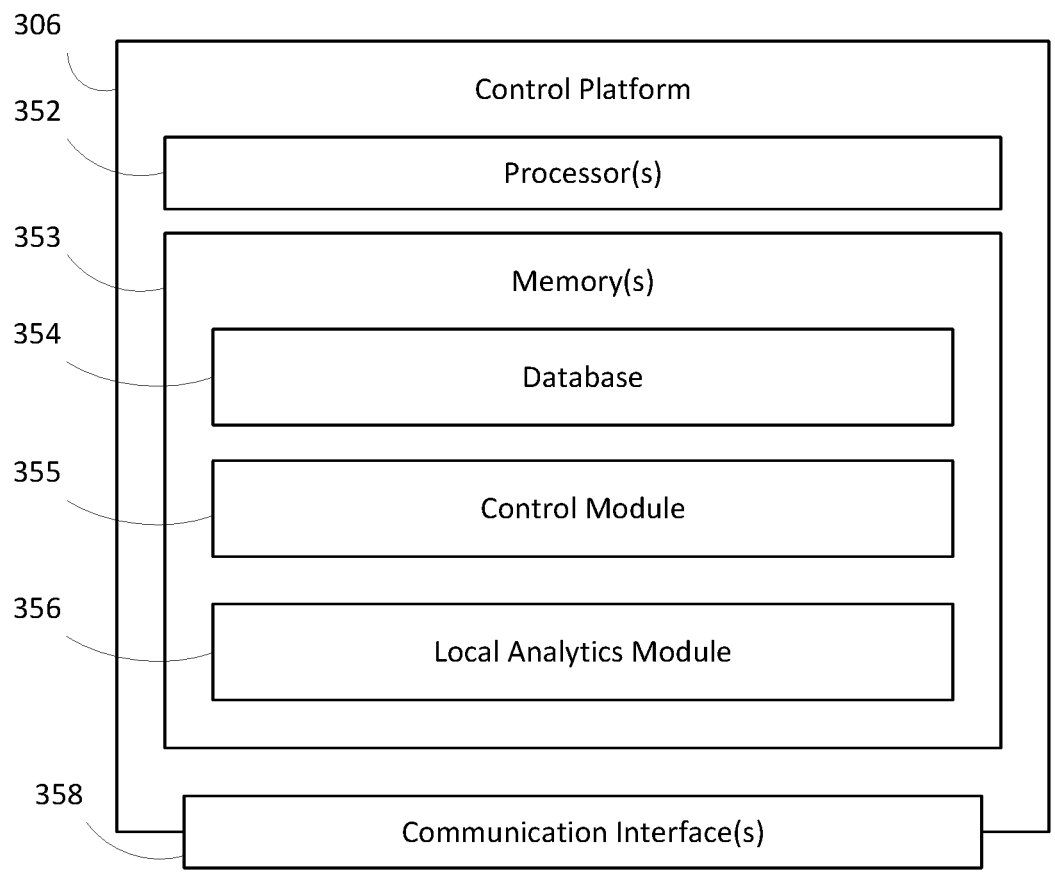
FIG. 3D depicts an illustrative control computing platform for analyzing data related to the operation of one or more pieces of equipment in a plant in accordance with one or more example embodiments.
Figure 3E:
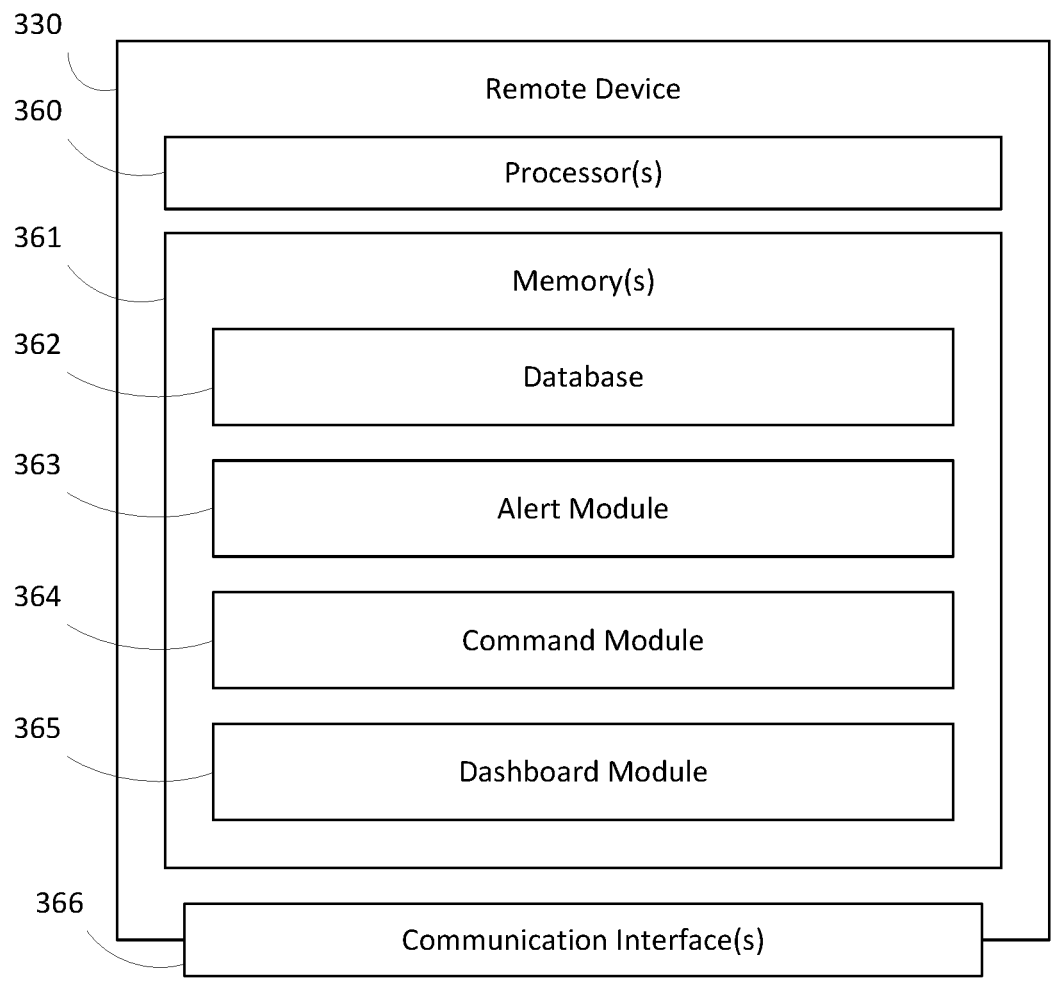
FIG. 3E depicts an illustrative remote computing device for receiving and sending alerts and information related to the operation of one or more pieces of equipment in a plant in accordance with one or more example embodiments.

The computing system environment 300 of FIG. 3A includes logical block diagrams of numerous platforms and devices that are further elaborated upon in FIG. 3B, FIG. 3C, FIG. 3D, and FIG. 3E. FIG. 3B is an illustrative data collection platform 302. FIG. 3C is an illustrative data analysis platform 304. FIG. 3D is an illustrative control platform 306. FIG. 3E is an illustrative remote device. These platforms and devices of FIG. 3 include one or more processing units (e.g., processors) to implement the methods and functions of certain aspects of the present disclosure in accordance with the example embodiments. The processors may include general-purpose microprocessors and/or special-purpose processors designed for particular computing system environments or configurations. For example, the processors may execute computer-executable instructions in the form of software and/or firmware stored in the memory of the platform or device. Examples of computing systems, environments, and/or configurations that may be suitable for use with the disclosed embodiments include, but are not limited to, personal computers (PCs), server computers, hand-held or laptop devices, smart phones, multiprocessor systems, microprocessor-based systems, programmable consumer electronics, network PCs, minicomputers, mainframe computers, virtual machines, distributed computing environments that include any of the above systems or devices, and the like.

In addition, the platform and/or devices in FIG. 3 may include one or more memories of a variety of computer-readable media. Computer-readable media may be any available media that may be accessed by the data collection platform, may be non-transitory, and may include volatile and nonvolatile, removable and non-removable media implemented in any method or technology for storage of information such as computer-readable instructions, object code, data structures, database records, program modules, or other data. Examples of computer-readable media may include random access memory (RAM), read only memory (ROM), electronically erasable programmable read only memory (EEPROM), flash memory or other memory technology, compact disk read-only memory (CD-ROM), digital versatile disks (DVD) or other optical disk storage, magnetic cassettes, magnetic tape, magnetic disk storage or other magnetic storage devices, or any other medium that can be used to store the desired information and that can be accessed by the data collection platform 302. The memories in the platform and/or devices may further store modules that may comprise compiled software code that causes the platform, device, and/or overall system to operate in a technologically improved manner as disclosed herein. For example, the memories may store software used by a computing platform, such as operating system, application programs, and/or associated database. Alternatively or additionally, a module may be implemented in a virtual machine or multiple virtual machines.

Furthermore, the platform and/or devices in FIG. 3 may include one or more communication interfaces including, but not limited to, a microphone, keypad, touch screen, and/or stylus through which a user of a computer (e.g., a remote device) may provide input, and may also include a speaker for providing audio output and a video display device for providing textual, audiovisual and/or graphical output. The communication interfaces may include a network controller for electronically communicating (e.g., wirelessly or wired) over a public network 310 or private network 308 with one or more other components on the network. The network controller may include electronic hardware for communicating over network protocols, including TCP/IP, UDP, Ethernet, and other protocols.

In some examples, one or more sensor devices in FIG. 3A may be enhanced by incorporating functionality that may otherwise be found in a data collection platform 302. These enhanced sensor system may provide further filtering of the measurements and readings collected from their sensor devices. For example, with some of the enhanced sensor systems in the operating environment illustrated in FIG. 3A, an increased amount of processing may occur at the sensor so as to reduce the amount of data needing to be transferred over a private network 308 in real-time to a computing platform. The enhanced sensor system may filter at the sensor itself the measured/collected/captured data and only particular, filtered data may be transmitted to the data collection platform 302 for storage and/or analysis.

Referring to FIG. 3B, in one example, a data collection platform 302 may comprise a processor 334, one or more memories 335, and communication interfaces 340. The memory 335 may comprise a database 336 for storing data records of various values collected from one or more sources. In addition, a data collection module 337 may be stored in the memory and assist the processor 334 in the data collection platform 302 in communicating with, via the communications interface, one or more sensor, measurement, and data capture systems, and processing the data received from these sources. In some embodiments, the data collection module may comprise computer-executable instructions that, when executed by the processor, cause the data collection platform to perform one or more of the steps disclosed herein. In other embodiments, the data collection module may be a hybrid of software-based and/or hardware-based instructions to perform one or more of the steps disclosed herein. In some examples, the data collection module may assist an enhanced sensor system with further filtering the measurements and readings collected from the sensor devices. In some examples, the data collection module 337 may receive some or all data from a plant or piece of equipment, and/or may provide that data to one or more other modules or servers.

Data collection platform 302 may include or be in communication with one or more data historians 338. The data historian 338 may be implemented as one or more software modules, one or more virtual machines, or one or more hardware elements (e.g., servers). The data historian 338 may collect data at regular intervals (e.g., every minute, every two minutes, every ten minutes, every thirty minutes).

The data historian 338 may include or be in communication with a process scout 339. The process scout 339 may be implemented as one or more software modules, one or more virtual machines, or one or more hardware elements (e.g., servers). The process scout 339 may work with or in place of the data collection module 337 and/or the data historian 338 to handle one or more aspects of data replication.

The data historian 338 may include or be in communication with one or more software modules, one or more virtual machines, or one or more hardware elements (e.g., servers) configured to work with or in place of the data collection module 337 and/or the data historian 338 to handle one or more aspects of data replication.

Although the elements of FIG. 3B are illustrated as logical block diagrams, the disclosure is not so limited. In particular, one or more of the logical boxes in FIG. 3B may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database in FIG. 3B is illustrated as being stored inside one or more memories in the data collection platform 302, FIG. 3B contemplates that the database may be stored in a standalone data store communicatively coupled to the data collection module and processor of the data collection platform via the communications interface of the data collection platform.

In addition, the data collection module 337 may assist the processor in the data collection platform 302 in communicating with, via the communications interface, and processing data received from other sources, such as data feeds from third-party servers and manual entry at the field site from a dashboard graphical user interface (e.g., dashboard 305, dashboard 313). For example, a third-party server may provide contemporaneous weather data to the data collection module. Some elements of chemical and petrochemical/refinery plants may be exposed to the outside and thus may be exposed to various environmental stresses. Such stresses may be weather related such as temperature extremes (hot and cold), high wind conditions, and precipitation conditions such as snow, ice, and rain. Other environmental conditions may be pollution particulates such as dust and pollen, or salt if located near an ocean, for example. Such stresses can affect the performance and lifetime of equipment in the plants. Different locations may have different environmental stresses. For example, a refinery in Texas will have different stresses than a chemical plant in Montana. In another example, data manually entered from a dashboard graphical user interface (or other means) may be collected and saved into memory by the data collection module. Production rates may be entered and saved in memory. Tracking production rates may indicate issues with flows. For example, as fouling occurs, the production rate may fall if a specific outlet temperature can no longer be achieved at the targeted capacity and capacity has to be reduced to maintain the targeted outlet temperature.

Referring to FIG. 3C, in one example, a data analysis platform 304 may comprise a processor 342, one or more memories 343, and communication interfaces 350. The memory 343 may comprise a database for storing data records of various values collected from one or more sources. Alternatively, the database may be the same database as that depicted in FIG. 3B and the data analysis platform 304 may communicatively couple with the database via the communication interface 350 of the data analysis platform 304. At least one advantage of sharing a database between the two platforms is the reduced memory requirements due to not duplicating the same or similar data.

In addition, the data analysis platform 304 may include a data acquisition tool 344. In some embodiments, the data acquisition tool 344 may comprise computer-executable instructions that, when executed by the processor 342, cause the data analysis platform 304 to perform one or more of the steps disclosed herein. In other embodiments, the data acquisition tool 344 may be a virtual machine. In some embodiments, the data acquisition tool 344 may be a hybrid of software-based and/or hardware-based instructions to perform one or more of the steps disclosed herein. The data acquisition tool 344 may collect data.

Further, the data analysis platform 304 may include a data service 345. In some embodiments, the data service 345 may comprise computer-executable instructions that, when executed by the processor, cause the data analysis platform 304 to perform one or more of the steps disclosed herein. In other embodiments, the data service 345 may be a virtual machine. In some embodiments, the data service 345 may be a hybrid of software-based and/or hardware-based instructions to perform one or more of the steps disclosed herein.

Also, the data analysis platform may include a data historian 346. In some embodiments, the data historian 346 may comprise computer-executable instructions that, when executed by the processor, cause the data analysis platform to perform one or more of the steps disclosed herein. In other embodiments, the data historian 346 may be a virtual machine. In some embodiments, the data historian 346 may be a hybrid of software-based and/or hardware-based instructions to perform one or more of the steps disclosed herein. The data historian 346 may collect data at regular intervals (e.g., every minute, every two minutes, every ten minutes, every thirty minutes).

Additionally, the data analysis platform 304 may include a data lake 347. In some embodiments, the data lake 347 may comprise computer-executable instructions that, when executed by the processor, cause the data analysis platform 304 to perform one or more of the steps disclosed herein. In other embodiments, the data lake 347 may be a virtual machine. In some embodiments, the data lake 347 may be a hybrid of software-based and/or hardware-based instructions to perform one or more of the steps disclosed herein. The data lake 347 may perform relational data storage. The data lake 347 may provide data in a format that may be useful for processing data and/or performing data analytics.

Moreover, the data analysis platform 304 may include a calculations service 348. In some embodiments, the calculations service may comprise computer-executable instructions that, when executed by the processor, cause the data analysis platform 304 to perform one or more of the steps disclosed herein. In other embodiments, the calculations service may be a virtual machine. In some embodiments, the calculations service 348 may be a hybrid of software-based and/or hardware-based instructions to perform one or more of the steps disclosed herein. The calculations service may collect data, perform calculations, and/or provide key performance indicators. The calculations service may implement, for example, process dynamic modeling software or tools (e.g., UniSim).

Furthermore, the data analysis platform 304 may include a utility service 349. In some embodiments, the utility service 349 may comprise computer-executable instructions that, when executed by the processor, cause the data analysis platform to perform one or more of the steps disclosed herein. In other embodiments, the utility service 349 may be a virtual machine. In some embodiments, the utility service 349 may be a hybrid of software-based and/or hardware-based instructions to perform one or more of the steps disclosed herein. The utility service 349 may take information from the calculations service 348 and put the information into the data lake. The utility service 349 may provide data aggregation service, such as taking all data for a particular range, normalizing the data (e.g., determining an average), and combining the normalized data into a file to send to another system or module.

One or more components of the data analysis platform 304 may assist the processor 342 in the data analysis platform 304 in processing and analyzing the data values stored in the database. In some embodiments, the data analysis platform 304 may perform statistical analysis, predictive analytics, and/or machine learning on the data values in the database to generate predictions and models. The data analysis platform 304 may compare temperature data from different dates to determine if changes are occurring. Such comparisons may be made on a monthly, weekly, daily, hourly, real-time, or some other basis.

Referring to FIG. 3C, the data analysis platform 304 may generate recommendations for adjusting one or more parameters for the operation of the plant environment depicted in FIG. 3A. In some embodiments, the data analysis platform 304 may, based on the recommendations, generate command codes that may be transmitted, via the communications interface, to cause adjustments or halting/starting of one or more operations in the plant environment. The command codes may be transmitted to a control platform for processing and/or execution. In an alternative embodiment, the command codes may be directly communicated, either wirelessly or in a wired fashion, to physical components at the plant, where the physical components comprise an interface to receive the commands and execute them.

Although the elements of FIG. 3C are illustrated as logical block diagrams, the disclosure is not so limited. In particular, one or more of the logical boxes in FIG. 3C may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database is visually depicted in FIG. 3C as being stored inside one or more memories in the data analysis platform, FIG. 3C contemplates that the database may be stored in a standalone data store communicatively coupled to the processor of the data analysis platform 304 via the communications interface of the data analysis platform 304. Furthermore, the databases from multiple plant locations may be shared and holistically analyzed to identify one or more trends and/or patterns in the operation and behavior of the plant and/or plant equipment. In such a crowdsourcing-type example, a distributed database arrangement may be provided where a logical database may simply serve as an interface through which multiple, separate databases may be accessed. As such, a computer with predictive analytic capabilities may access the logical database to analyze, recommend, and/or predict the behavior of one or more aspects of plants and/or equipment. In another example, the data values from a database from each plant may be combined and/or collated into a single database where predictive analytic engines may perform calculations and prediction models.

Referring to FIG. 3D, in one example, a control platform 306 may comprise a processor 352, one or more memories 353, and communication interfaces 358. The memory 353 may comprise a database 354 for storing data records of various values transmitted from a user interface, computing device, or other platform. The values may comprise parameter values for particular equipment at the plant. For example, some illustrative equipment at the plant that may be configured and/or controlled by the control platform include, but is not limited to, a feed switcher, sprayer, one or more valves 329, one or more pumps 328, one or more gates, and/or one or more drains. In addition, a control module 355 may be stored in the memory 353 and assist the processor 352 in the control platform 306 in receiving, storing, and transmitting the data values stored in the database 354. In some embodiments, the control module 355 may comprise computer-executable instructions that, when executed by the processor, cause the control platform 306 to perform one or more of the steps disclosed herein. In other embodiments, the control module 355 may be a hybrid of software-based and/or hardware-based instructions to perform one or more of the steps disclosed herein.

In a plant environment such as illustrated in FIG. 3A, if sensor data is outside of a safe range, this may be cause for immediate danger. As such, there may be a real-time component to the system such that the system processes and responds in a timely manner. Although in some embodiments, data could be collected and leisurely analyzed over a lengthy period of months, numerous embodiments contemplate a real-time or near real-time responsiveness in analyzing and generating alerts, such as those generated or received by the alert module in FIG. 3E.

Referring to FIG. 3E, in one example, a remote device 330 may comprise a processor 360, one or more memories 361, and communication interfaces 366. The memory 361 may comprise a database 362 for storing data records of various values entered by a user or received through the communications interface. In addition, an alert module 363, command module 364, and/or dashboard module 365 may be stored in the memory 361 and assist the processor 360 in the remote device 330 in processing and analyzing the data values stored in the database 362. In some embodiments, the aforementioned modules may comprise computer-executable instructions that, when executed by the processor, cause the remote device 330 to perform one or more of the steps disclosed herein. In other embodiments, the aforementioned modules may be a hybrid of software-based and/or hardware-based instructions to perform one or more of the steps disclosed herein. In some embodiments, the aforementioned modules may generate alerts based on values received through the communications interface. The values may indicate a dangerous condition or even merely a warning condition due to odd sensor readings. The command module 364 in the remote device 330 may generate a command that, when transmitted through the communications interface to the platforms at the plant, causes adjusting of one or more parameter operations of the plant environment depicted in FIG. 3A. In some embodiments, the dashboard module 365 may display a graphical user interface to a user of the remote device 330 to enable the user to enter desired parameters and/or commands. These parameters/commands may be transmitted to the command module 364 to generate the appropriate resulting command codes that may be then transmitted, via the communications interface 366, to cause adjustments or halting/starting of one or more operations in the plant environment. The command codes may be transmitted to a control platform for processing and/or execution. In an alternative embodiment, the command codes may be directly communicated, either wirelessly or in a wired fashion, to physical components at the plant such that the physical components comprise an interface to receive the commands and execute them.

Although FIG. 3E is not so limited, in some embodiments the remote device 330 may comprise a desktop computer, a smartphone, a wireless device, a tablet computer, a laptop computer, and/or the like. The remote device may be physically located locally or remotely, and may be connected by one of communications links to the public network that is linked via a communications link to the private network. The network used to connect the remote device may be any suitable computer network including the Internet, an intranet, a wide-area network (WAN), a local-area network (LAN), a wireless network, a digital subscriber line (DSL) network, a frame relay network, an asynchronous transfer mode (ATM) network, a virtual private network (VPN), or any combination of any of the same. Communications links may be any communications links suitable for communicating between workstations and server, such as network links, dial-up links, wireless links, hard-wired links, as well as network types developed in the future, and the like. Various protocols such as transmission control protocol/Internet protocol (TCP/IP), Ethernet, file transfer protocol (FTP), hypertext transfer protocol (HTTP) and the like may be used, and the system can be operated in a client-server configuration to permit a user to retrieve web pages from a web-based server. Any of various conventional web browsers can be used to display and manipulate data on web pages.

Although the elements of FIG. 3E are illustrated as logical block diagrams, the disclosure is not so limited. In particular, one or more of the logical boxes in FIG. 3E may be combined into a single logical box or the functionality performed by a single logical box may be divided across multiple existing or new logical boxes. Moreover, some logical boxes that are visually presented as being inside of another logical box may be moved such that they are partially or completely residing outside of that logical box. For example, while the database is visually depicted in FIG. 3E as being stored inside one or more memories in the remote device, FIG. 3E contemplates that the database may be stored in a standalone data store communicatively coupled, via the communications interface, to the modules stored at the remote device and processor of the remote device.

Referring to FIG. 3, in some examples, the performance of operation in a plant may be improved by using a cloud computing infrastructure and associated methods, as described in U.S. Patent Application Publication No. 2016/0260041, which was published Sep. 8, 2016, and which is herein incorporated by reference in its entirety. The methods may include, in some examples, obtaining plant operation information from the plant and/or generating a plant process model using the plant operation information. The method may include receiving plant operation information over the Internet, or other computer network (including those described herein) and automatically generating a plant process model using the plant operation information. These plant process models may be configured and used to monitor, predict, and/or optimize performance of individual process units, operating blocks and/or complete processing systems. Routine and frequent analysis of predicted versus actual performance may further allow early identification of operational discrepancies that may be acted upon to optimize impact, including financial or other impact.

The aforementioned cloud computing infrastructure may use a data collection platform 302 (such as software that performs data collection at a plant site) associated with a plant to capture data, e.g., sensor measurements, which may be automatically sent to the cloud infrastructure, which may be remotely located, where the data may be reviewed to, for example, eliminate errors and biases, and used to calculate and report performance results. The data collection platform 302 may include an optimization unit that acquires data from a customer site, other site, and/or plant (e.g., sensors and other data collectors at a plant) on a recurring basis. For cleansing, the data may be analyzed for completeness and corrected for gross errors by the optimization unit. The data may also be corrected for measurement issues (e.g., an accuracy problem for establishing a simulation steady state) and overall mass balance closure to generate a duplicate set of reconciled plant data. The corrected data may be used as an input to a simulation process, in which the process model is tuned to ensure that the simulation process matches the reconciled plant data. An output of the reconciled plant data may be used to generate predicted data using a collection of virtual process model objects as a unit of process design.

The performance of the plant and/or individual process units of the plant may be compared to the performance predicted by one or more process models to identify any operating differences or gaps. Furthermore, the process models and collected data (e.g., plant operation information) may be used to run optimization routines that converge on an optimal plant operation for a given values of, e.g., feed, products, and/or prices. A routine may be understood to refer to a sequence of computer programs or instructions for performing a particular task.

The data analysis platform 304 may comprise an analysis unit that determines operating status, based on at least one of a kinetic model, a parametric model, an analytical tool, and a related knowledge and best practice standard. The analysis unit may receive historical and/or current performance data from one or a plurality of plants to proactively predict future actions to be performed. To predict various limits of a particular process and stay within the acceptable range of limits, the analysis unit may determine target operational parameters of a final product based on actual current and/or historical operational parameters. This evaluation by the analysis unit may be used to proactively predict future actions to be performed. In another example, the analysis unit may establish a boundary or threshold of an operating parameter of the plant based on at least one of an existing limit or an operation condition. In yet another example, the analysis unit may establish a relationship between at least two operational parameters related to a specific process for the operation of the plant. Finally, in yet another example, one or more of the aforementioned examples may be performed with or without a combination of the other examples.

The plant process model may predict plant performance that is expected based upon plant operation information. The plant process model results can be used to monitor the health of the plant and to determine whether any upset or poor measurement occurred. The plant process model may be generated by an iterative process that models at various plant constraints to determine the desired plant process model.

Using a web-based system for implementing the method of this disclosure may provide one or more benefits, such as improved plant economic performance due to an increased ability by plant operators to identify and capture economic opportunities, a sustained ability to bridge plant performance gaps, and an increased ability to leverage personnel expertise and improve training and development. Some of the methods disclosed herein allow for automated daily evaluation of process performance, thereby increasing the frequency of performance review with less time and effort required from plant operations staff.

Further, the analytics unit may be partially or fully automated. In one or more embodiments, the system may be performed by a computer system, such as a third-party computer system, remote from the plant and/or the plant planning center. The system may receive signals and parameters via the communication network, and displays in real time related performance information on an interactive display device accessible to an operator or user. The web-based platform allows all users to work with the same information, thereby creating a collaborative environment for sharing best practices or for troubleshooting. The method further provides more accurate prediction and optimization results due to fully configured models. Routine automated evaluation of plant planning and operation models allows timely plant model tuning to reduce or eliminate gaps between plant models and the actual plant performance. Implementing the aforementioned methods using the web-based platform also allows for monitoring and updating multiple sites, thereby better enabling facility planners to propose realistic optimal targets.

FIGS. 4A-4B depict illustrative system flow diagrams in accordance with one or more embodiments described herein. As shown in FIG. 4A, in step 401, data collection platform may collect sensor data. In step 402, data collection platform may transmit sensor data to data analysis platform. In step 403, data analysis platform may analyze data. In step 404, data analysis platform may update one or more dashboards.

As shown in FIG. 4B, in step 405, data analysis platform may send an alert to remote device 1 and/or remote device 2. In step 406, data analysis platform may receive a command from remote device 1 and/or remote device 2. In some embodiments, the control platform may receive the command from remote device 1 and/or remote device 2. In step 407, data analysis platform may send a command to control platform. In some embodiments, the command may be similar to the command received from remote device 1 and/or remote device 2. In some embodiments, data analysis platform may perform additional analysis based on the received command from remote device 1 and/or remote device 2 before sending a command to control platform. In step 408, control platform may adjust an operating parameter. The adjusting the operating parameter may be based on the command received from data analysis platform, remote device 1, and/or remote device 2. The adjusting the operating parameter may be related to one or more pieces of equipment (e.g., reactors, separators, chloride treaters) associated with sensors that collected the sensor data in step 401. For example, a flow rate may be increased or decreased, a valve may be opened or closed, a process may be started, stopped, extended, or shortened, or the like.

Detecting and Addressing Problems with Chloride Treaters

Aspects of the present disclosure are directed to monitoring catalytic reforming processes for potential and existing issues, providing alerts, and/or adjusting operating conditions. One or more process performance indicators may be monitored including, but not limited to, reactants, products, temperature, and/or pressure.

In some embodiments, the system may suggest adjusting or may automatically adjust one or more operating conditions. Alternatively or additionally, the system may provide an alert or other information to a device associated with an operator, with a request to adjust the one or more operating conditions. For example, the system may adjust the flow of reactants into a reactor, a temperature of a part of the reactor, a pressure of a part of the reactor, or the like.

Adjusting the operating characteristics may be performed in an iterative fashion. Periodically, the system may determine whether there is a difference between a recommended operating condition and an actual operating condition, and if so, again adjust one or more operating conditions to decrease the difference. By iteratively reviewing recent performance and adjusting conditions, the system may thereby improve the operating performance.

Processing Sensor Data

One or more calculations may be performed for chloride treater remote monitoring service. These calculations may assist in alerting and helping diagnose the status of the adsorbent.

The data processing platform may receive (e.g., from one or more sensors) one or more operational parameters of the catalytic reforming process, which may be used alone or in combination for determining the status of the adsorbent.

The data processing platform may use one or more design parameters, alone or in combination, for determining the status of the chloride treater. A design parameter may be a level at which the chloride treater was designed to operate at, below, or above.

In some instances, the timestamp of a calculated attribute may match the timestamp of the raw data used for the calculation. In some instances, a calculated attribute may use one or more results of one or more other calculated attributes; therefore, the order in which the attributes are calculated may be relevant.

In some embodiments, raw values may be checked for bad values. If bad values are detected, the data processing platform may either skip calculation or replace the bad value with NULL, as appropriate for subsequent calculations. For averages, a provision may be made to skip bad/null values and/or timestamps.

Some units of measurement for variables may be specified. Some variables may be dimensionless, and therefore might not have a defined unit of measurement.

Dashboard

Figure 6:
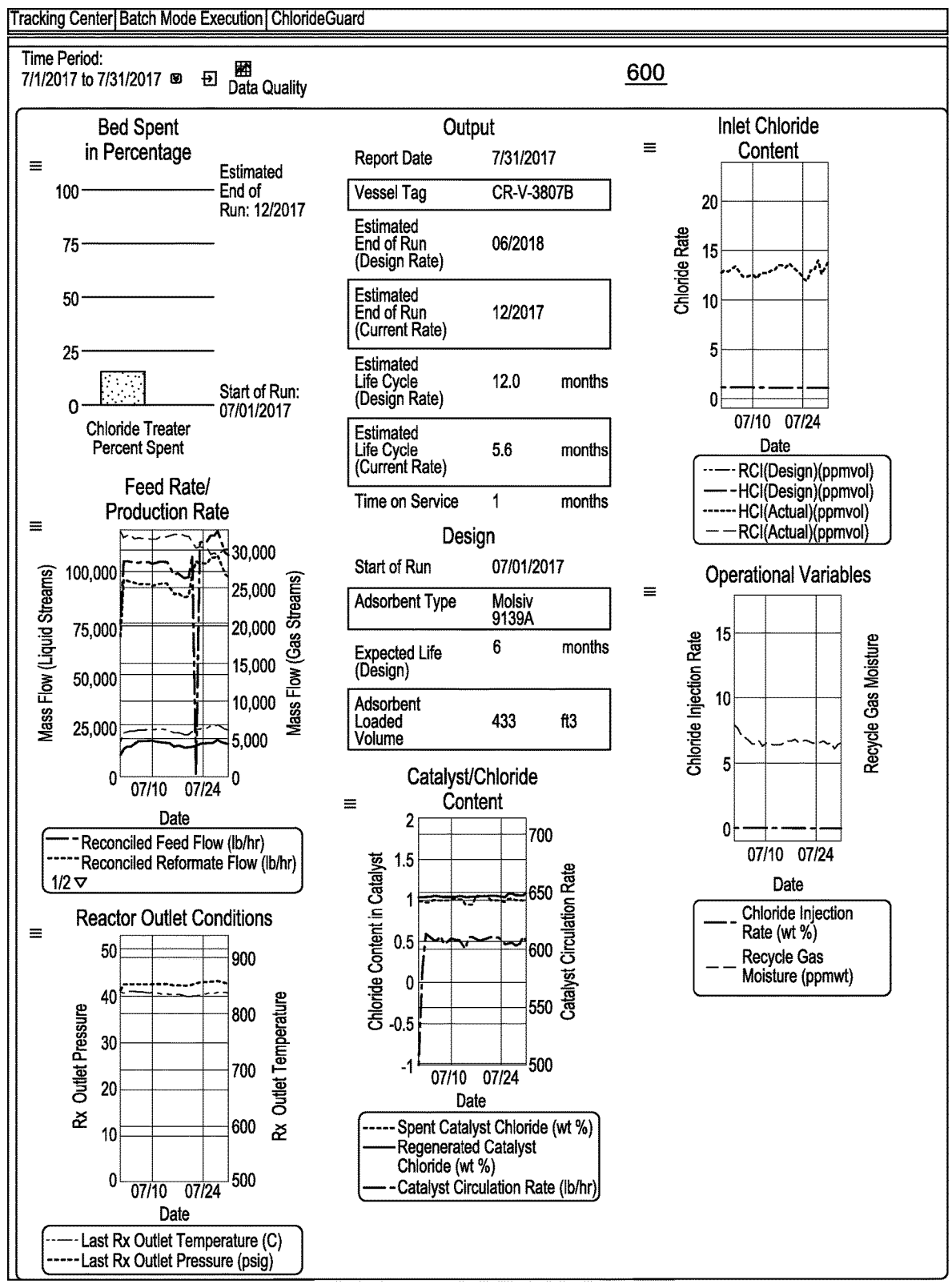
FIG. 6 depicts an illustrative dashboard for viewing information and/or taking actions related to one or more aspects of a plant operation in accordance with one or more example embodiments.

FIG. 6 depicts an illustrative dashboard 600 that may include information about the operation of a catalytic reforming process utilizing one or more chloride treaters and in accordance with one or more aspects described herein. The dashboard may include or be a part of one or more graphical user interfaces of one or more applications that may provide information received from one or more sensors or determined based on analyzing information received from one or more sensors, according to one or more embodiments described herein. The dashboard may be part of a smartphone application (e.g., running on a remote device, such as remote device 1 or remote device 2), a desktop application, a web application (e.g., that runs in a web browser), a web site, an application running on a plant computer, or the like.

The dashboard may be different based on an intended user of the dashboard. For example, as depicted in FIG. 3A, one or more systems (e.g., the data analysis platform, the client portal) may interface with a dashboard (e.g., dashboard 305, dashboard 313). The data analysis platform dashboard may provide the same or different information, charts, graphs, buttons, functions, or the like, as the client portal dashboard. The system may determine a user identify based on a user profile, a user login, a device identifier, a device address, or the like.

Returning to FIG. 6, the dashboard may include one or more visual representations of data (e.g., chart, graph) that shows information about a plant, a particular piece of equipment in a plant, a process performed by a plant, or a particular piece or combination of equipment in the plant. For example, one or more graphs may show information about a feed rate, a production rate, a catalyst rate, a chloride rate, a chloride content in a solid, liquid or gas, a gas concentration level, a product level, a temperature, a pressure, an operating condition, an efficiency, a production level, bed spent, operational variables, or the like. The dashboard may include a description of the equipment, the combination of equipment, or the plant to which the visual display of information pertains.

The dashboard may display the information for a particular time or period of time (e.g., the last five minutes, the last ten minutes, the last hour, the last two hours, the last 12 hours, the last 24 hours, multiple days, multiple months). The dashboard may be adjustable to show different ranges of time, automatically or based on user input.

The dashboard may include a contact name and/or contact information (e.g., telephone number, pager number, email address, text message number, social media account name) for a sales representative. Then, for example, if a dashboard user needs assistance (e.g., purchasing more adsorbent, seeking assistance for repairs, finding out more information about purchased products), the dashboard user may easily contact the sales representative.

The dashboard may include a contact name and/or contact information for technical support. Then, for example, if the dashboard user using the dashboard needs assistance (e.g., seeking assistance for repairs, interpreting dashboard data, adjusting a product level, adjusting an equipment setting, adjusting an operating characteristic), the dashboard user may easily contact technical support.

The dashboard may display a time and/or date range of the time and/or date range for which data is being displayed. For example, the period may be one month. The displayed time period (e.g., to one week, two weeks, three weeks, four weeks) may be changed. Specifically, a pop-up window may be triggered (e.g., by selecting an interface option, such as a drop-down arrow). The pop-up window may allow selection of a time period (e.g., years, quarters, months, weeks, days, hours, minutes) for displaying data. The pop-up window may allow selection of a range of data for a selected time (e.g., previous week, this week, next week, last x number of weeks, next x number of weeks, week to date).

The dashboard may include, on one or more graphs, a line indicating a design level. Specifically, the line may indicate the level at which the equipment was designed to operate. The design line may be static. The design line may be based on an actual operating condition of another factor. For example, the design line for emission levels of a first matter may be based on the actual operating level of a second matter. The design line may be provided by, e.g., an entity associated with a design of the equipment, the plant, or the like.

The dashboard may include, on one or more graphs, a line, bar, or other indicator of an actual operating result. The actual operating result may be related to a time and/or date range (e.g., the displayed time and/or date range). The actual operating result may be related to a particular chloride treater (e.g., dark blue for a first chloride treater, medium blue for a second chloride treater, light blue for a third chloride treater). The actual operating result may be dynamic.

The dashboard may include one or more colored banners or graphic elements (e.g., at the bottom of the dashboard or bar graph) that may correspond to one or more current operating conditions corresponding to one or more graphs of the dashboard. The colored banners or graphic elements may include one or more colors (e.g., green, yellow, red), which may correspond to one or more operating conditions of chloride treater equipment. For example, if a chloride level of an adsorbent bed of a chloride treater is at an acceptable level, the colored banner or graphic element may be a first color (e.g., green). If the chloride level of the adsorbent bed is at a level that necessitates increased monitoring or that may indicate an impending need (e.g., maintenance or replacement), the colored banner or graphic element may be a second color (e.g., yellow). If the chloride level is at a problematic level, the colored banner or graphic element may be a third color (e.g., red).

The dashboard may include a graph that shows feed rate into a reactor and production rates out of the reactor over a time period (e.g., a month). Colored lines may indicate feed flow and reformate flow by volume (e.g., barrel/day).

The dashboard may include a graph that shows inlet chloride load of a particular (X) treater over a time period (e.g., a month). For example, inlet organic chlorides flow rates (lb/hr) (design) and feed rates (lb/hr) (actual) may be indicated by different colored lines. Likewise, inlet HCL flow rates (lb/hr) (design) and feed rates (lb/hr) (actual) may be indicated by different colored lines.

The dashboard may include a graph that shows catalyst circulation rates, and chloride content/chloride rate in catalysts over a time period (e.g., a month). Colored lines may indicate spent catalyst chloride (wt %), regenerated catalyst chloride (wt %), catalysts circulation rate (lb/hr), chloride rate in spent catalyst (lb/hr), and chloride rate in regenerated catalyst The dashboard may include a bar graph indicating percentage spent of an adsorbent bed at a given moment in time. This graph may provide an easy-to-read visual indication of the life of the bed. A color of the graph may correspond to a lifespan of the bed. For example, if the bed has a first percentage life remaining (e.g., under a first threshold), the graph may be green. If the bed has a second percentage life remaining (e.g., over the first threshold but under a second threshold), the graph may be yellow. If the bed has a third percentage life remaining (e.g., over the first threshold and the second threshold), the graph may be red, and so on. A color or other visual indicator on the dashboard may provide an indication of whether the adsorbent bed is spent or at or near the end of its life (e.g., if the graph is red, the adsorbent bed may be at or near the end of its life).

The dashboard may include a graph that shows various operational variables over a time period (e.g., a month). For example, colored lines may indicate chloride injection rate (wt %), last Rx outlet pressure (kPag), recycle gas moisture (ppmwt), and/or last Rx outlet temperature (C).

The dashboard may provide certain plant configuration information, such as chloride treater adsorbent type, loaded volume, date loaded, and/or expected adsorbent life (design) (e.g., in months).

The dashboard may provide certain outputs including chloride treater time on service, estimated life cycle design rate and current rate, the current date, adsorbent estimated end of run design rate, and/or current rate.

One or more of the graphs may include a first line that indicates an ideal or desired level, and a second line that indicates an actual operating level. The graph may correspond with a colored banner at the bottom of the screen. The banner may indicate if the chloride level is within in a suitable range (e.g., green), an elevated but acceptable range (e.g., yellow), or is out of range (e.g., red).

In some embodiments, the dashboard may include an operational summary over a time period, e.g., yearly.

In some aspects, data displayed by the dashboard may be refreshed in real time, according to a preset schedule (e.g., every five seconds, every ten seconds, every minute), and/or in response to a refresh request received from a user.

The dashboard may include a button or option that allows a user to send data to one or more other devices. For example, the user may be able to send data via email, SMS, text message, iMessage, FTP, cloud sharing, AirDrop, or some other method. The user may be able to select one or more pieces of data, graphics, charts, graphs, elements of the display, or the like to share or send.

The data collected by this system may provide historical information of events, operations, and/or data. This information can be modelled to predict and/or anticipate future issues. This can be used to recommend or call for proactive maintenance actions and/or make corrective actions to the operation of the process unit to have an uninterrupted service.

Alerts

In some embodiments, a graphical user interface of an application may be used for providing alerts and/or receiving or generating commands for taking corrective action related to chloride treatment units, in accordance with one or more embodiments described herein. The graphical user interface may include an alert with information about a current state of a piece of equipment (e.g., a chloride treater), a problem being experienced by a piece of equipment (e.g., adsorbent), a problem with a plant, or the like. For example, the graphical user interface may include an alert that a chloride treater is experiencing a particular issue, a chloride treater is operating at a particular level, a particular problem has been detected, or another alert.

The graphical user interface may include one or more buttons that, when pressed, cause one or more actions to be taken. For example, the graphical user interface may include a button that, when pressed, causes an operating characteristic (e.g., of a chloride treater, of a valve, of a plant, or the like) to change. For example, an amount of chemical being used may be increased or decreased (e.g., the computer may send a signal that opens or closes one or more valves or adjusts one or more flow controllers) in response to a particular condition being detected. In another example, the graphical user interface may include a button that, when pressed, sends an alert to a contact, the alert including information similar to the information included in the alert provided via the graphical user interface. For example, an alert may be sent to one or more devices. In response to an alert, the one or more devices may receive user input that may cause those devices to send alerts, further information, and/or instructions to one or more other devices. In a further example, the graphical user interface may include a button that, when pressed, shows one or more other actions that may be taken (e.g., additional corrective actions, adjustments to operating conditions).

Several levels of alerts may be used. One level of alerts may be for alerts that require emergency action (e.g., Level 1). Another level of alerts may be for alerts that require action, but not immediate action (e.g., Level 2). Another level of alerts may be for alerts that are not related to the chloride treater (e.g., Level 3). A number of illustrative alerts are described below. These alerts are merely illustrative, and the disclosure is not limited to these alerts. Instead, these are merely examples of some of the types of alerts that may be related to, e.g., a chloride treater unit. As exemplified below, the alerts may identify the problem or issue and/or what corrective action (if any) may or should be taken.

An alert may include an indication of the alert level (e.g., level 1, level 2, level 3). The alert may include a name or identifier of the alert. The name or descriptive identifier of the alert may include a description of the determined problem that the alert is based on. The alert may include information on the determined problem. The alert may include information about potential causes of the determined problem. The alert may include a recommended further action (e.g., investigate and contact service representative). The alert may include information about who has received the alert. The alert may include an error code and/or error description for the error. The alert may include potential consequences of the error. The alert may include suggested actions for resolving the error.

CONCLUSION

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one or more of the steps illustrated in the illustrative figures may be performed in other than the recited order, and one or more depicted steps may be optional in accordance with aspects of the disclosure.

What is claimed is:

1. A method comprising:
    receiving, by a data analysis computing device, sensor data collected by a sensor associated with a chloride treater in a plant having a catalytic reforming reactor with a chloride containing catalyst, the chloride treater receiving a stream of product from the catalytic reforming reactor, the stream of product containing chloride contaminants, the sensor data relating to the chloride contaminants;
    analyzing the sensor data to determine a current operating condition for the chloride treater;
    determining a difference between the current operating condition for the chloride treater and a recommended operating condition for the chloride treater;
    based on the analyzed sensor data, determining a recommended adjustment for an operating parameter of the plant to reduce the difference between the current operating condition and the recommended operating condition;
    displaying the difference between the current operating condition and the recommended operating condition on a dashboard;
    sending a command implementing the recommended adjustment for the operating parameter of the plant; and,
    receiving, by the data analysis computing device, sensor data collected by the sensor associated with the chloride treater at the recommended operating condition.

2. The method of claim 1, comprising:
    displaying, on the dashboard, more than one recommendations for adjusting operating parameters of the plant, the more than one recommendation including the recommended adjustment.

3. The method of claim 1, comprising:
    determining an estimated end of life of the chloride treater based on an estimated chloride treater current operating condition and estimated chloride treater past operating conditions.

4. The method of claim 1, comprising:
    determining an estimated end of life of the chloride treater based on a measured chloride treater current operating condition and measured chloride treater past operating conditions.

5. The method of claim 1, comprising:
    determining an estimated end of life of the chloride treater based on at least one of an estimated chloride treater current operating condition, an estimated chloride treater past operating condition, a measured chloride treater current operating condition, or a measured chloride treater past operating condition.

6. The method of claim 1, comprising:
    generating an alarm based on the sensor data exceeding a threshold.

7. The method of claim 1, comprising:
    determining a recommended proactive maintenance action for the chloride treater.

* * * * *